(12) United States Patent
Daw et al.

(10) Patent No.: US 7,976,540 B2
(45) Date of Patent: Jul. 12, 2011

(54) ELECTROSURGICAL MEDICAL SYSTEM AND METHOD

(75) Inventors: Derek Daw, Costa Mesa, CA (US);
James Huntington Dabney, Irvine, CA (US)

(73) Assignee: Senorx, Inc., Irvine, CA (US)

( * ) Notice: Subject to any disclaimer, the term of this patent is extended or adjusted under 35 U.S.C. 154(b) by 12 days.

(21) Appl. No.: 12/229,789

(22) Filed: Aug. 27, 2008

(65) Prior Publication Data

US 2009/0088736 A1  Apr. 2, 2009

Related U.S. Application Data

(60) Division of application No. 11/297,652, filed on Dec. 7, 2005, which is a continuation-in-part of application No. 11/703,861, filed on Feb. 8, 2007, which is a division of application No. 10/658,572, filed on Sep. 9, 2003, now Pat. No. 7,175,618, which is a division of application No. 09/752,978, filed on Dec. 28, 2000, now Pat. No. 6,620,157.

(60) Provisional application No. 60/475,747, filed on Jun. 3, 2003.

(51) Int. Cl.
*A61B 18/10* (2006.01)
(52) U.S. Cl. ............... 606/34; 606/39; 606/40
(58) Field of Classification Search .......... 606/32, 606/34–35, 37–39
See application file for complete search history.

(56) References Cited

U.S. PATENT DOCUMENTS

| 4,517,976 | A | | 5/1985 | Murakoshi et al. | |
|---|---|---|---|---|---|
| 4,559,943 | A | * | 12/1985 | Bowers | 606/37 |
| 4,658,819 | A | | 4/1987 | Harris et al. | |
| 4,739,759 | A | | 4/1988 | Rexroth et al. | |
| 4,878,493 | A | | 11/1989 | Pasternak et al. | |
| 5,087,257 | A | * | 2/1992 | Farin et al. | 606/35 |
| 5,159,929 | A | | 11/1992 | Morris et al. | |
| 5,269,780 | A | * | 12/1993 | Roos | 606/42 |

(Continued)

FOREIGN PATENT DOCUMENTS

DE       37 03 218       8/1988

(Continued)

OTHER PUBLICATIONS

*Force FX™ Electrosurgical Generator Instant Response to Tissue Density*, Instant Response Technology, http://www.valleylab.com/PRODUCTS/fx.htm, electrosurgical Generators pp. 1-4.

(Continued)

Primary Examiner — Michael Peffley
Assistant Examiner — Samantha Good

(57) ABSTRACT

A medical device system and method provide an RF electrosurgical generator coupled to an electrosurgical electrode via a patient box disposed in close proximity to the patient. An RF signal is delivered from the generator to the patient box where signal power is increased and the RF signal delivered to the electrosurgical electrode. The patient box is coupled to the electrosurgical electrode by a short cable capable of carrying an HV, high frequency 5 MHz signal without leakage. An electrical characteristic associated with the electrosurgical electrode is monitored and a desired RF power output and duty cycle maintained by adjusting DC input voltage applied to an RF amplifier, responsive to the monitoring. The system determines when the electrosurgical cutting electrode has started cutting and switches from a start mode to a run mode having a different RF duty cycle and a reduced RF power output controlled by a servo system.

4 Claims, 19 Drawing Sheets

U.S. PATENT DOCUMENTS

| | | | |
|---|---|---|---|
| 5,300,068 A * | 4/1994 | Rosar et al. | 606/34 |
| 5,445,635 A * | 8/1995 | Denen et al. | 606/27 |
| 5,507,743 A | 4/1996 | Edwards et al. | |
| 5,558,671 A * | 9/1996 | Yates | 606/38 |
| 5,617,857 A | 4/1997 | Chader et al. | |
| 5,749,869 A | 5/1998 | Lindenmeier et al. | |
| 5,772,659 A * | 6/1998 | Becker et al. | 606/34 |
| 5,849,009 A | 12/1998 | Bernaz | |
| 5,971,980 A * | 10/1999 | Sherman | 606/34 |
| 5,976,128 A | 11/1999 | Schilling et al. | |
| 5,997,535 A | 12/1999 | Betsill et al. | |
| 6,022,347 A | 2/2000 | Lindenmeier et al. | |
| 6,036,681 A | 3/2000 | Hooven | |
| 6,066,134 A | 5/2000 | Eggers et al. | |
| 6,074,386 A * | 6/2000 | Goble et al. | 606/34 |
| 6,162,216 A | 12/2000 | Guziak et al. | |
| 6,228,080 B1 * | 5/2001 | Gines | 606/34 |
| 6,391,024 B1 | 5/2002 | Sun et al. | |
| 6,432,065 B1 | 8/2002 | Burdorff et al. | |
| 6,458,121 B1 | 10/2002 | Rosenstock et al. | |
| 6,475,215 B1 * | 11/2002 | Tanrisever | 606/45 |
| 6,514,248 B1 | 2/2003 | Edwards et al. | |
| 6,632,183 B2 | 10/2003 | Bowman et al. | |
| 6,939,347 B2 * | 9/2005 | Thompson | 606/34 |
| 6,981,941 B2 | 1/2006 | Whitman et al. | |
| 7,060,063 B2 | 6/2006 | Marion et al. | |
| 2003/0055419 A1 * | 3/2003 | Panescu et al. | 606/34 |
| 2003/0130711 A1 | 7/2003 | Pearson et al. | |
| 2003/0144605 A1 | 7/2003 | Burbank et al. | |
| 2003/0171745 A1 * | 9/2003 | Francischelli et al. | 606/41 |
| 2003/0181898 A1 | 9/2003 | Bowers | |
| 2004/0030334 A1 | 2/2004 | Quick et al. | |
| 2004/0082945 A1 | 4/2004 | Clague et al. | |
| 2004/0181219 A1 | 9/2004 | Goble et al. | |
| 2005/0119646 A1 | 6/2005 | Scholl et al. | |

FOREIGN PATENT DOCUMENTS

| | | |
|---|---|---|
| EP | 0 225 973 | 6/1987 |
| EP | 1 051 948 | 11/2000 |
| EP | 1 053 720 | 11/2000 |
| EP | 1 082 945 | 3/2001 |
| EP | 1 157 667 | 11/2001 |
| EP | 1 519 472 | 3/2005 |
| EP | 1 527 743 | 5/2005 |
| GB | 2 146 534 | 4/1985 |
| JP | 2002 320325 | 10/2002 |
| WO | WO 93/15655 | 8/1993 |
| WO | WO 96/39088 | 12/1996 |
| WO | WO 98/07378 | 2/1998 |
| WO | WO 2004/110294 | 12/2004 |
| WO | WO 2005/060849 | 7/2005 |

OTHER PUBLICATIONS

*New! Force EZ™ Electrosurgical Generator Instant Response to tissue Density*, Instant Response Technology, http://www.valleylab.com/PRODUCTS/fx.htm, Electrosurgical Generators pp. 1-4.

*Amplifiermodule 1-30MHz 150Watts*, LCF Enterprises RF Power Amplifiers, www.lcfamps.com, pp. 1-2.

* cited by examiner ns application is a divisional of copending application Ser. No. 11/297,652, filed Dec. 7, 2005, which a continuation-in-part of application Ser. No. 11/703,861 filed Feb. 8, 2007, which is a divisional of Ser. No. 10/658,572 filed Sep. 9, 2003, now U.S. Pat. No. 7,175,618, which is a divisional of Ser. No. 09/752,978 filed Dec. 28, 2000, now U.S. Pat. No. 6,620,157 from all which priority is claimed. This application is related to U.S. application Ser. No. 10/847,699, filed May 17, 2004 and U.S. Provisional Application Ser. No. 60/475,747, filed Jun. 3, 2003, the contents of each of which are hereby incorporated by reference as if set forth in their entireties. This application is also related to application Ser. No. 12/229,793, application Ser. No. 12/229,794 and application Ser. No. 12/229,801, all of which are filed concurrently and all of which claim the same priority as in the aforementioned.

ELECTROSURGICAL MEDICAL SYSTEM AND METHOD

RELATED APPLICATIONS

This application is a divisional of copending application Ser. No. 11/297,652, filed Dec. 7, 2005, which a continuation-in-part of application Ser. No. 11/703,861 filed Feb. 8, 2007, which is a divisional of Ser. No. 10/658,572 filed Sep. 9, 2003, now U.S. Pat. No. 7,175,618, which is a divisional of Ser. No. 09/752,978 filed Dec. 28, 2000, now U.S. Pat. No. 6,620,157 from all which priority is claimed. This application is related to U.S. application Ser. No. 10/847,699, filed May 17, 2004 and U.S. Provisional Application Ser. No. 60/475,747, filed Jun. 3, 2003, the contents of each of which are hereby incorporated by reference as if set forth in their entireties. This application is also related to application Ser. No. 12/229,793, application Ser. No. 12/229,794 and application Ser. No. 12/229,801, all of which are filed concurrently and all of which claim the same priority as in the aforementioned.

FIELD OF THE INVENTION

The present invention relates to an electrosurgical method and system including an electrosurgical generator and an electrosurgical electrode.

BACKGROUND

Typical electrosurgical procedures, such as cutting or cautery procedures, are performed with a handheld device which the user can manipulate and control as the RF energy is delivered to the electrosurgical electrode in order to facilitate the creation of the desired effect at the electrosurgical electrode which performs the cutting or cautery procedure. As disclosed in U.S. patent application Ser. No. 10/714,126 issued to Marion, et al., it would be advantageous to have an automated method to evaluate effects at the electrode and to automatically adjust RF characteristics at the electrode based on such feedback. Such a feedback procedure is clearly preferred to a method that relies upon the user to sense and feel a change in cutting characteristics while cutting with the electrosurgical electrode. For example, different tissue impedances and cutting electrode contact areas affect the voltage and current required to cut and require adjustment to the RF power supplied to the electrode. To rely on the user's impression of the cutting quality to adjust cutting parameters would not be the most efficient way to optimize the cutting or cauterizing operation.

Furthermore, starting a cut is a different process than the actual cutting process and can require different control parameters than the cutting operation. Typical electrosurgical generator/electrode systems do not distinguish between starting a cut and cutting and do not provide different controls for these different modes of operation. It would therefore be advantageous to provide an electrosurgical electrode/generator system that does differentiate between the two aforementioned modes to provide desired control capabilities in each.

Another concern in RF electrosurgical electrode/generator systems is the different cutting characteristics required by different tissue types. For example, certain tissue types require high RF power outputs to efficiently cut the tissue. In particular, some tissue types require a high RF output voltage but do not require high average power to sustain cutting. Simply controlling the RF output voltage and current, however, is not sufficient to support all tissue types and combinations of tissue types. Further, more custom tailored controls are needed.

Leakage currents, inadvertent currents between an electronic device and earth ground, are a serious concern in RF devices such as an RF electrosurgical generator/electrode system. It would be desirable to prevent or at least mitigate such leakage currents. Since inadvertent contact between the patient and earth ground can cause undesirable leakage currents, it would logically be advantageous to provide an electrosurgical electrode/generator system with leakage path detection capabilities.

In summary, it would be desirable to provide an electrosurgical electrode/generator system capable of detecting the difference between cutting mode and a start-to-cut mode and providing separate controls and feedback systems in each mode. It would further be desirable to provide controls with novel and efficient telemetry systems that provide feedback and control of the cutting or cauterizing operation based upon monitoring characteristics at the electrode. It would further be desirable to mitigate leakage and to detect leakage paths when leakage does occur. The present invention addresses these and other needs.

SUMMARY OF THE INVENTION

To address these and other needs and in view of its purposes, the invention provides a medical device system including an electrosurgical generator and method for operating and controlling the electrosurgical generator to perform operations on a patient.

According to one aspect, RF power is delivered from an electrosurgical generator to an electrosurgical electrode being used on a patient. The method and system comprise providing an RF electrosurgical generator in a generator housing and a patient box in a patient box housing, the patient box housing disposed in close proximity to the patient and the generator housing disposed further from the patient than the patient box housing. An RF signal with a first RF power is delivered from the electrosurgical generator to the patient box. RF power of the RF signal is increased in the patient box and the RF signal with an increased RF power is delivered to the electrosurgical electrode as an RF output. The patient box is coupled to the electrosurgical electrode by a cable not greater than 2 meters long.

According to another aspect, a method and system for controlling an electrosurgical electrode of a medical device comprise delivering energy from an RF generator to an electrosurgical electrode, the RF generator including an RF amplifier; monitoring an electrical characteristic associated with the electrosurgical electrode; and maintaining a desired RF power output and a desired RF duty cycle by adjusting DC input voltage applied to an output stage of the RF amplifier based on the monitoring.

According to another aspect, a method and system for controlling an electrosurgical cutting electrode of a medical device provide for delivering energy from an RF generator to an electrosurgical cutting electrode; determining when the electrosurgical cutting electrode has started cutting tissue; and switching the delivering energy from a start mode that provides a relatively high RF power output and a first RF duty cycle, to a run mode having a second RF duty cycle and a reduced RF power output controlled by a control system servo responsive to the determining when cutting has started.

According to another aspect, a method and system for mitigating leakage in an RF electrosurgical generator provide for delivering an RF signal from an RF electrosurgical generator to an electrosurgical electrode by way of a patient box. The RF electrosurgical generator includes an RF amplifier. A balanced and symmetrical shielded transmission line couples the electrosurgical generator disposed in a first housing to the patient box disposed in a second, different housing. A common mode choke is included in the patient box. The common mode choke includes an output winding and a return winding, each winding wound about a ferrite core, the output winding and the return winding spaced apart and in parallel to maintain a desired impedance, the output winding comprising a wire carrying the RF signal as an output signal and the return winding comprising a duality of intertwined wires carrying a return signal from a return electrode, each winding having adjacent ribs spaced apart. A common mode signal is directed from the RF signal to the common mode choke thereby blocking the common mode signal.

BRIEF DESCRIPTION OF THE DRAWING

The present invention is best understood from the following detailed description when read in conjunction with the accompanying drawing. It is emphasized that, according to common practice, the various features of the drawing are not necessarily to scale. On the contrary, the dimensions of the various features are arbitrarily expanded or reduced for clarity. Like numerals denote like features throughout the specification and drawing.

DETAILED DESCRIPTION

The present invention provides an electrosurgical electrode/generator system that includes an electrosurgical electrode and an electrosurgical generator (ESG) with a very high reserve power capability. The system can carry out cutting and cautery functions and the cautery function is accomplished with high voltage sine waves rather than waveforms with high crest factors. This means that the electrosurgical generator can sustain high output voltage and current simultaneously over time—its power output is about three times greater than a typical electrosurgical generator in one exemplary embodiment.

Figure 1:
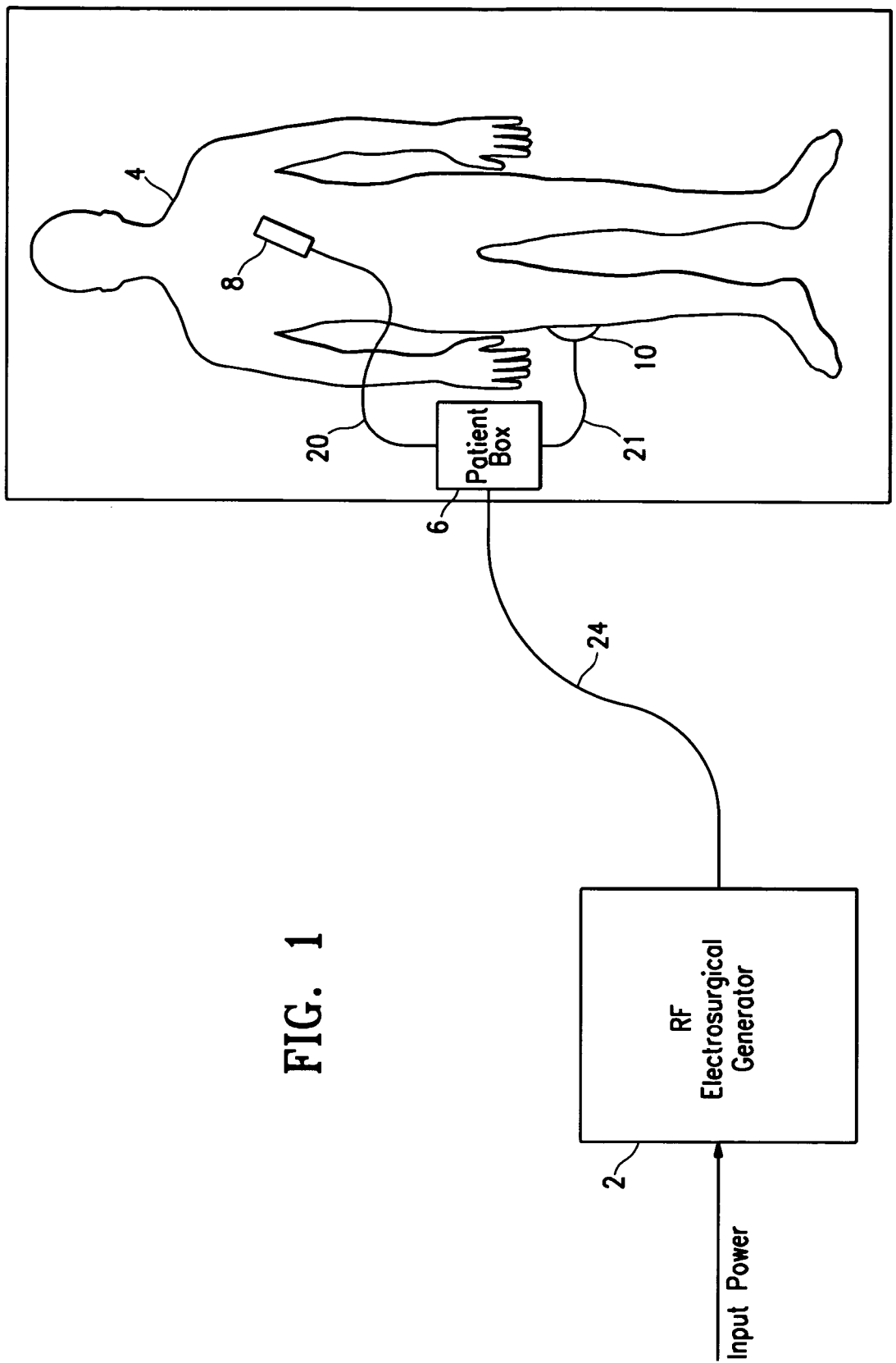
FIG. 1 is a schematic view showing the electrosurgical generator/electrode of the invention being used to perform a procedure on a patient.

FIG. 1 is a schematic diagram of an exemplary system and shows electrosurgical generator 2 being used to perform an operation on patient 4. The system includes patient box 6 coupled to electrosurgical generator 2. Electrosurgical generator 2 is an RF generator. Two RF outputs extend from patient box 6: one RF output provided to scalpel or electrosurgical electrode 8 and one to return electrode 10.

Patient box 6 is located in close proximity to patient 4. In the illustrated embodiment, patient box 6 lies on the operating table immediately next to patient 4. In another exemplary embodiment, patient box 6 may rest between the legs of patient 4. Electrosurgical generator 2 is located at a more distant location from patient 4. This arrangement provides the advantage that a high voltage, HV, high frequency (high MHz) signal can be delivered to patient 4 with minimal loss of RF power due to the antenna effect associated with a long wire. An RF signal is provided from electrosurgical generator 2 to patient box 6 via cable 24. Cable 24 may be a relatively long cable allowing electrosurgical generator 2 to be located at a distance of 10 meters or more from patient 4. In one embodiment, electrosurgical generator 2 may be disposed in another room. The RF output delivered from electrosurgical generator 2 to electrosurgical electrode 8 is stepped-up in patient box 6 by means of a transformer disposed within patient box 6. In other words, the RF power of the RF signal delivered from patient box 6 to electrosurgical electrode 8 is greater than the RF power of the signal delivered from electrosurgical generator 2 to patient box 6. In this manner, a high power signal can be delivered to electrosurgical electrode 8 without much loss due to antenna effect because cable 20 is the only cable that carries the stepped-up high voltage, high frequency RF signal and cable 20 is relatively short because of the proximity between patient box 6 and patient 4. In one embodiment, cable 20 may be 2 meters or less, and may preferably be 1 meter or less. Similarly, cable 21 connecting return electrode 10 to patient box 6 may be of similarly short dimension.

This arrangement enables the inventive electrosurgical generator to limit leakage current even though operating at high operating frequencies of about 5 megahertz and providing high output power. In a conventional electrosurgical generator arrangement, there is no patient box and the output of the electrosurgical generator comes directly from a panel of the generator and connects to the patient and cutting electrode via a long paired cable which may be 3 meters long or longer. While this may be usable at low frequencies (0.5 to 2 MHz) it causes leakage currents at high frequencies such as frequencies in the 5 MHz range. This type of cable connection in conventional technology is not balanced and provides capacitive and inductive leakage pads and additionally, the long wire connection provides a large antenna area for radiated leakage. To mitigate against such leakage currents, electrosurgical generator 2 includes a balanced output. The balanced output is provided by transformer coupling the RF output from the electrosurgical generator to the patient box using a shielded balanced transmission line. RF output is isolated from ground and any leakage to ground is identical for both output and return conductors. Since these two signals have opposite phases, the leakage currents cancel. This will be discussed in further detail below.

Figure 2A:
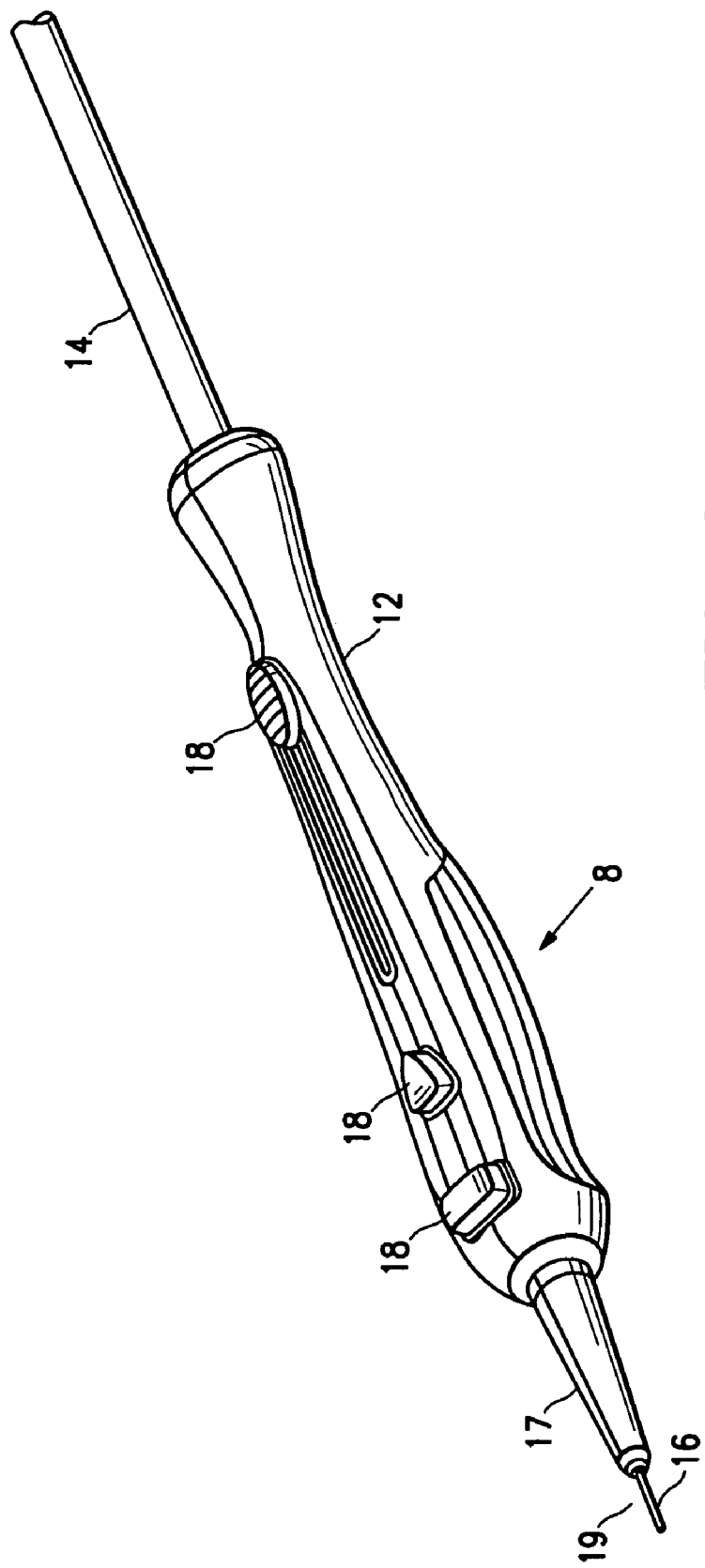
FIGS. 2A-2C show various embodiments of the electrosurgical electrode of the invention.
Figure 2B:
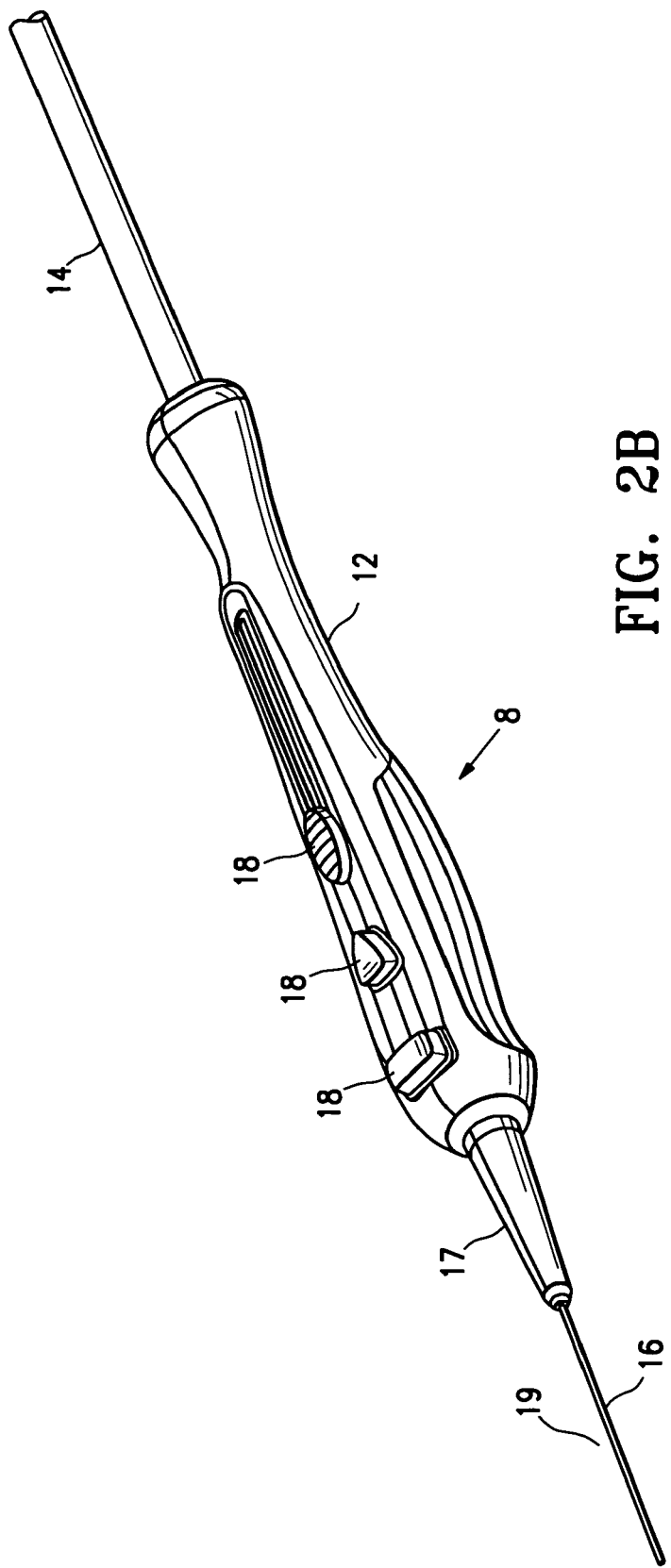
Figure 2C:
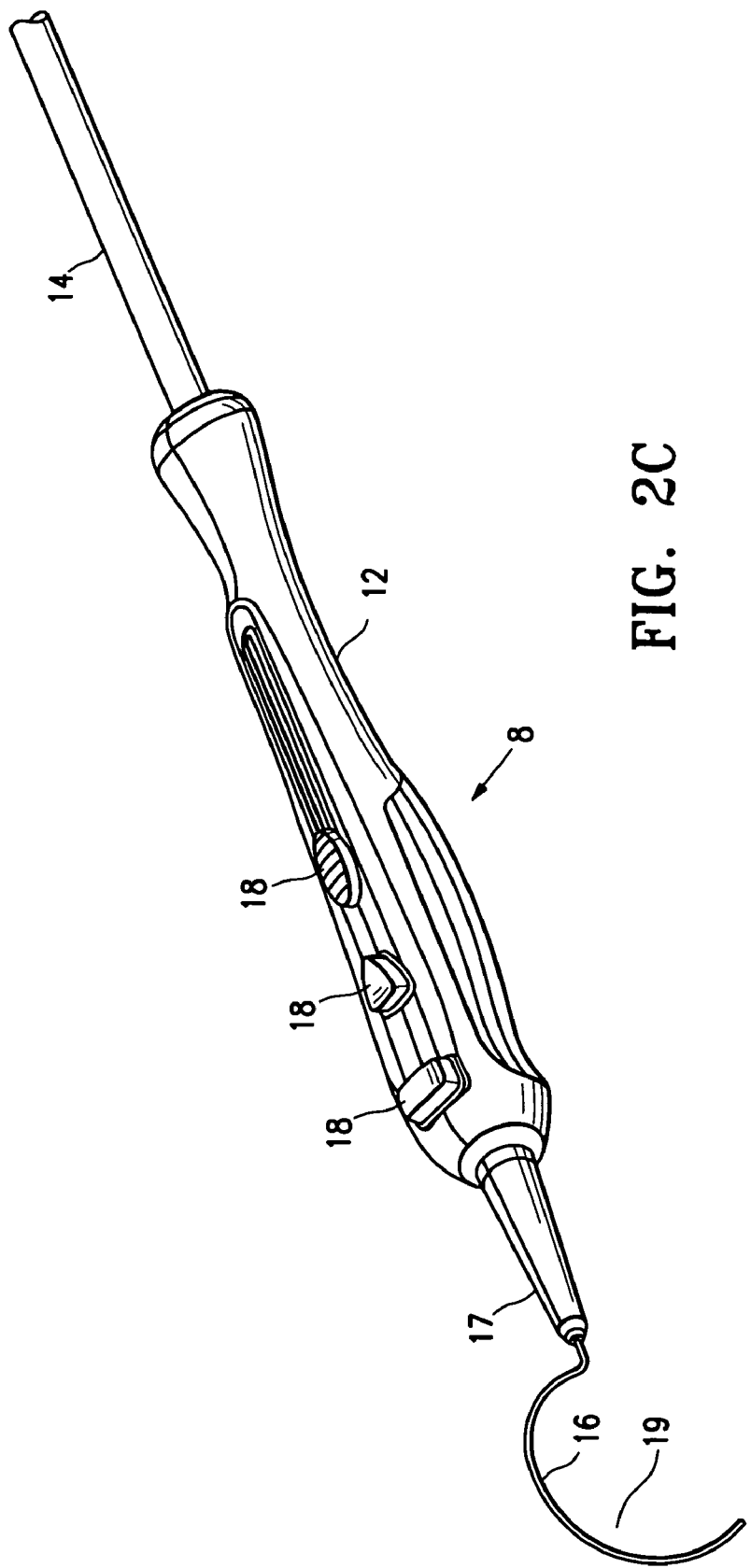

FIGS. 2A-2C are perspective views showing various exemplary embodiments of scalpel/electrosurgical electrode 8. Electrosurgical electrode 8 includes hand piece or housing 12, input power line 14, cutting probe 16 extending from nose piece 17 and mechanical controls 18. Cutting probe 16 is the electrode. When initiating a cut, a plasma is formed in vicinity 19 of cutting probe 16.

FIGS. 2A-2C show different exemplary configurations of cutting probe 16. Other configurations may be used as well. Each of the exemplary cutting electrodes shown in FIGS. 2A-2C is exemplary and the cutting probe 16, housing 12 and mechanical controls 18 may take on other shapes and locations in other exemplary embodiments.

One aspect of the invention provides a method and system for controlling the electrosurgical electrode of a medical device by delivering energy from the RF generator to the electrosurgical electrode. The RF generator includes an RF amplifier. An electrical characteristic associated with the electrosurgical electrode is monitored. A desired RF output level and a desired RF duty cycle is maintained by adjusting DC input voltage applied to an output stage of the RF amplifier based on monitoring the electrical characteristic.

Another aspect of the method and system of the invention is leakage current detection. An RF signal is delivered from an RF electrosurgical generator to an electrosurgical electrode by way of a patient box, the patient box and the RF electrosurgical generator disposed in separate housings such as shown in FIG. 1. A leakage current is detected by inducing a test signal in the patient box. This is done by directing the RF signal through an RF transformer in the patient box, coupling a series of two capacitors between ground and a center tap of a winding in the RF transformer, and inducing the test signal onto RF output leads of the patient box by passing the RF signal through a common mode transformer. The test signal has a frequency of about 500 kilohertz. According to one aspect, a balanced and symmetrical shielded transmission line couples the electrosurgical generator to the patient box by way of the transformer. The patient box may include a common mode choke. The common mode choke includes an output winding and a return winding, each wound about a ferrite core. The output winding and return winding are spaced apart and in parallel to maintain a desired impedance. The output winding is formed of a wire carrying the RF signal and the return winding includes intertwined wires. Each winding includes spaced-apart adjacent ribs. A common mode signal from the RF signal is directed to the common mode choke thereby blocking the common mode signal while allowing the output signal to be applied substantially unaltered to a patient.

The electrosurgical cutting electrode may be controlled in different operational modes. Energy is delivered from an RF generator to an electrosurgical cutting electrode. It is determined when the electrosurgical electrode has started cutting tissue and, when this is determined, the energy delivery system is switched from a start mode that provides a relatively high RF power output and a first RF duty cycle, to a run mode having a second RF duty cycle and a reduced RF power output that is controlled by a servo system. A matching unit is used to control the system during the start mode.

Further details of these aspects are discussed in reference to the following figures.

Figure 3:
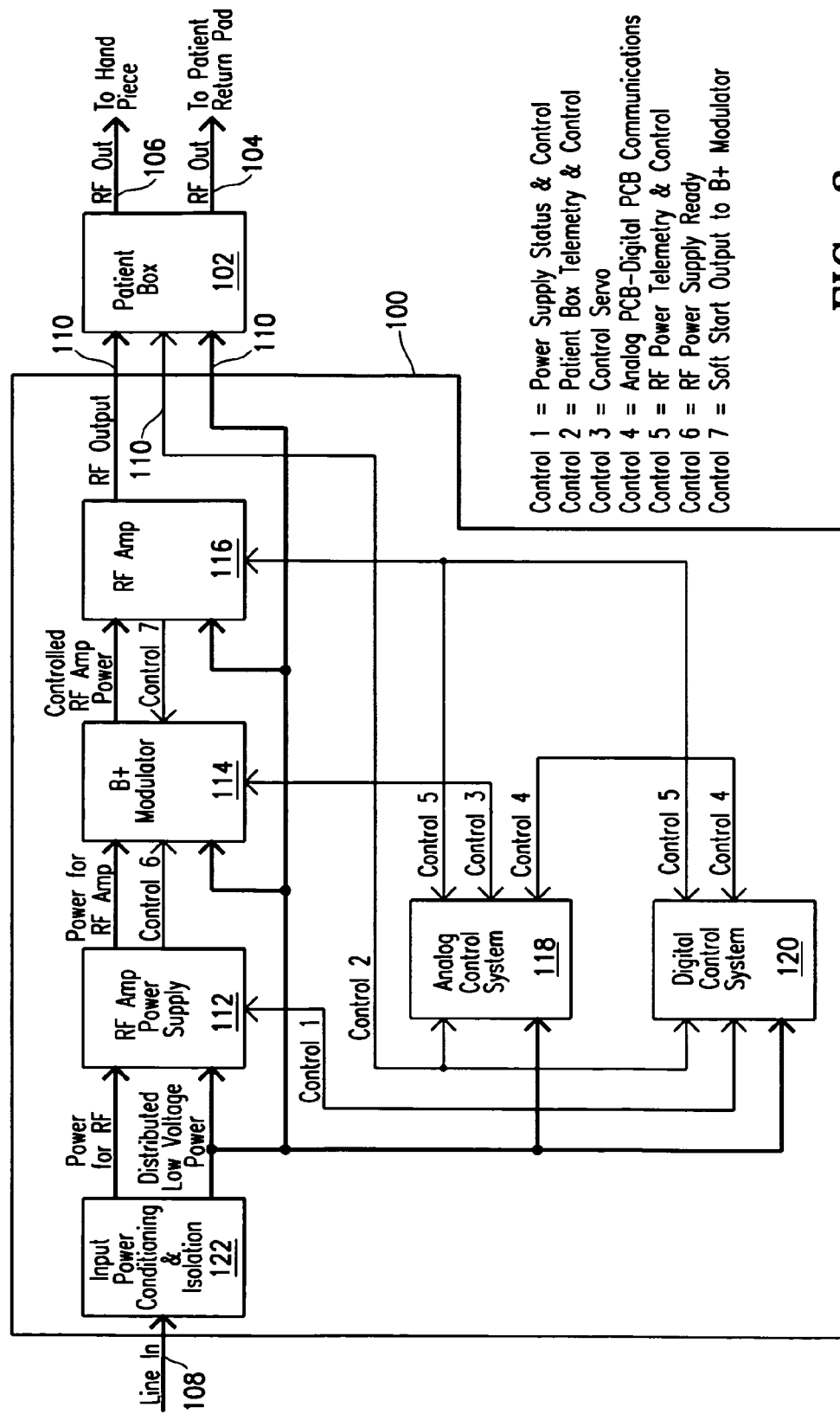
FIG. 3 is a block diagram of an exemplary electrosurgical generator system of the invention.
Figure 4:
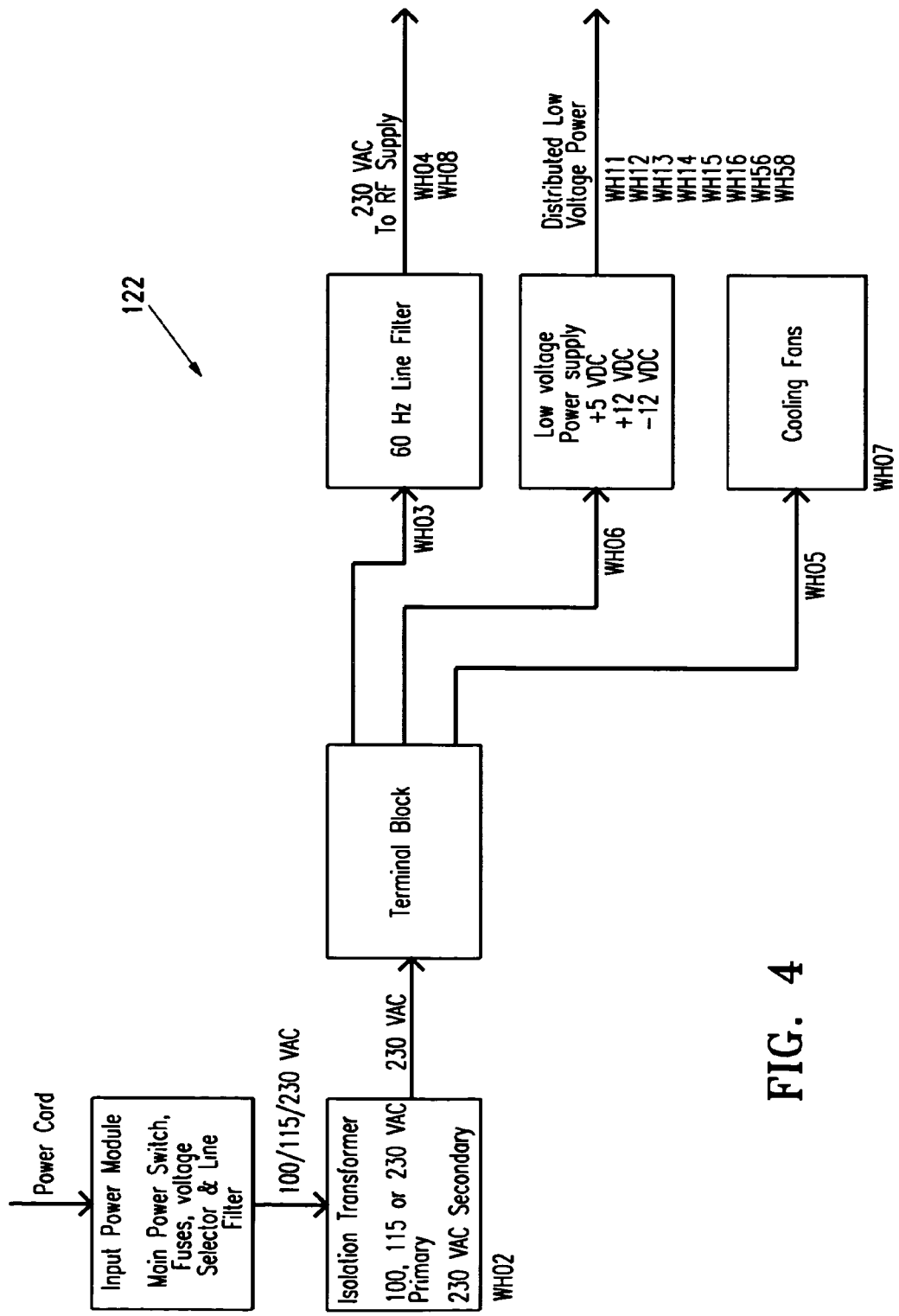
FIG. 4 is a block diagram showing input power conditioning and isolation in the electrosurgical generator system of the invention.
Figure 5:
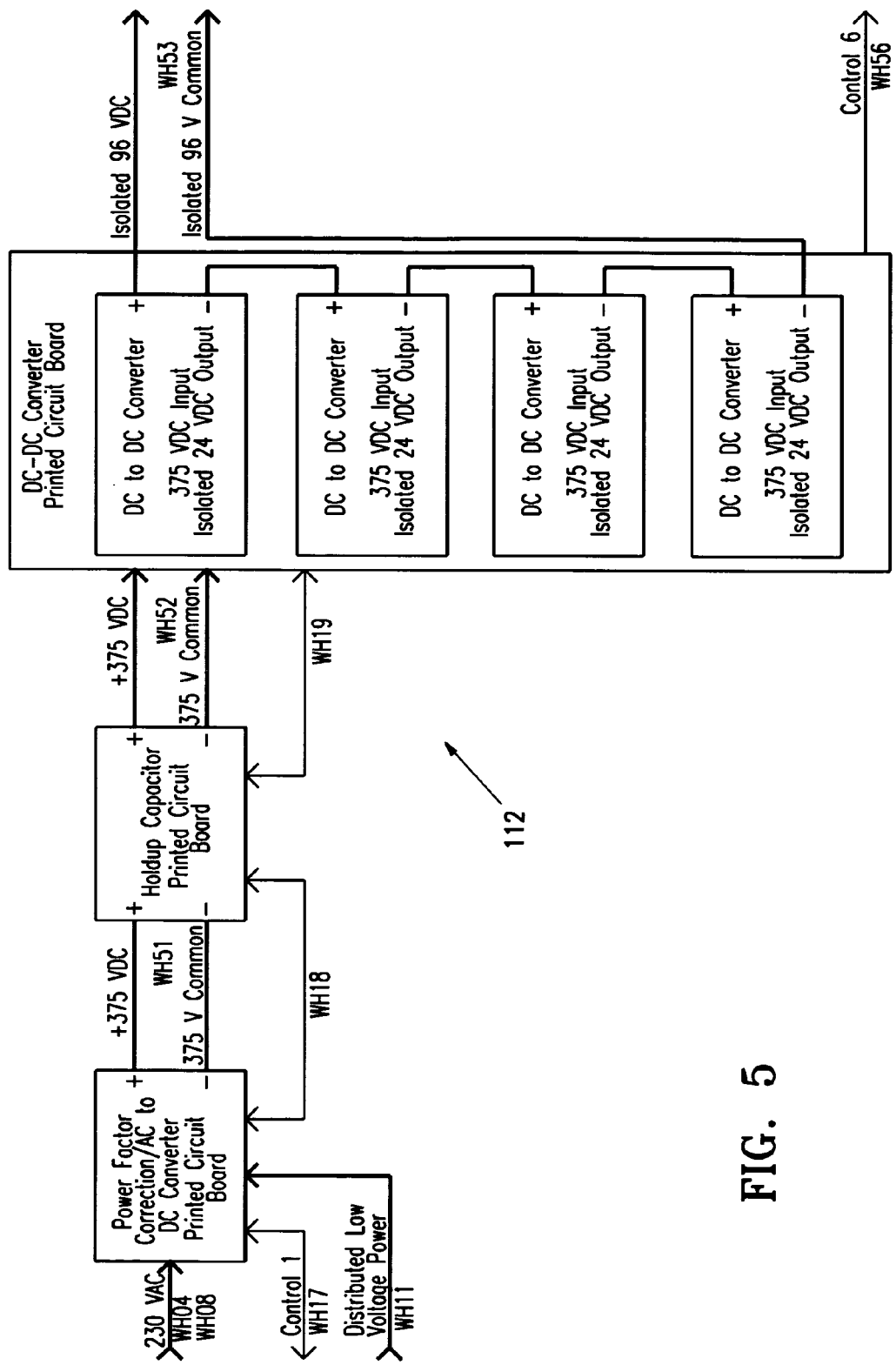
FIG. 5 is a block diagram showing the RF amp power supply in the electrosurgical generator system of the invention.
Figure 6:
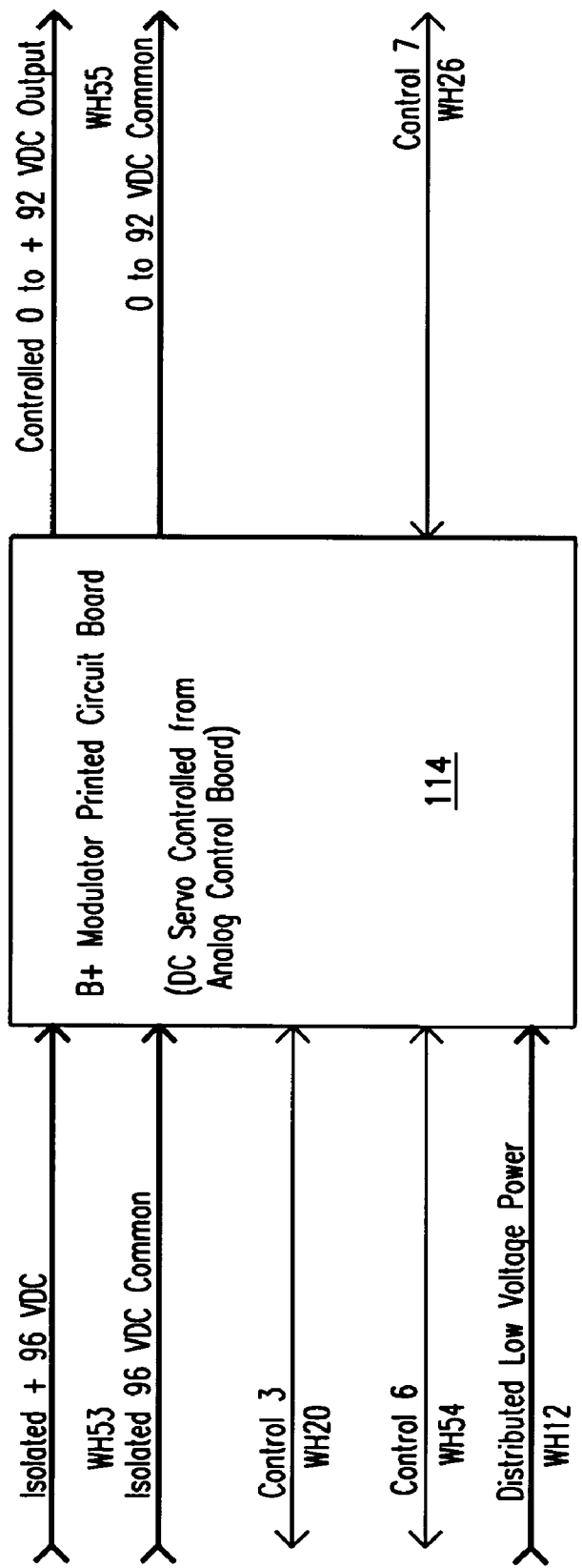
FIG. 6 is a block diagram showing a B+ modulator in the electrosurgical generator system of the invention.
Figure 7:
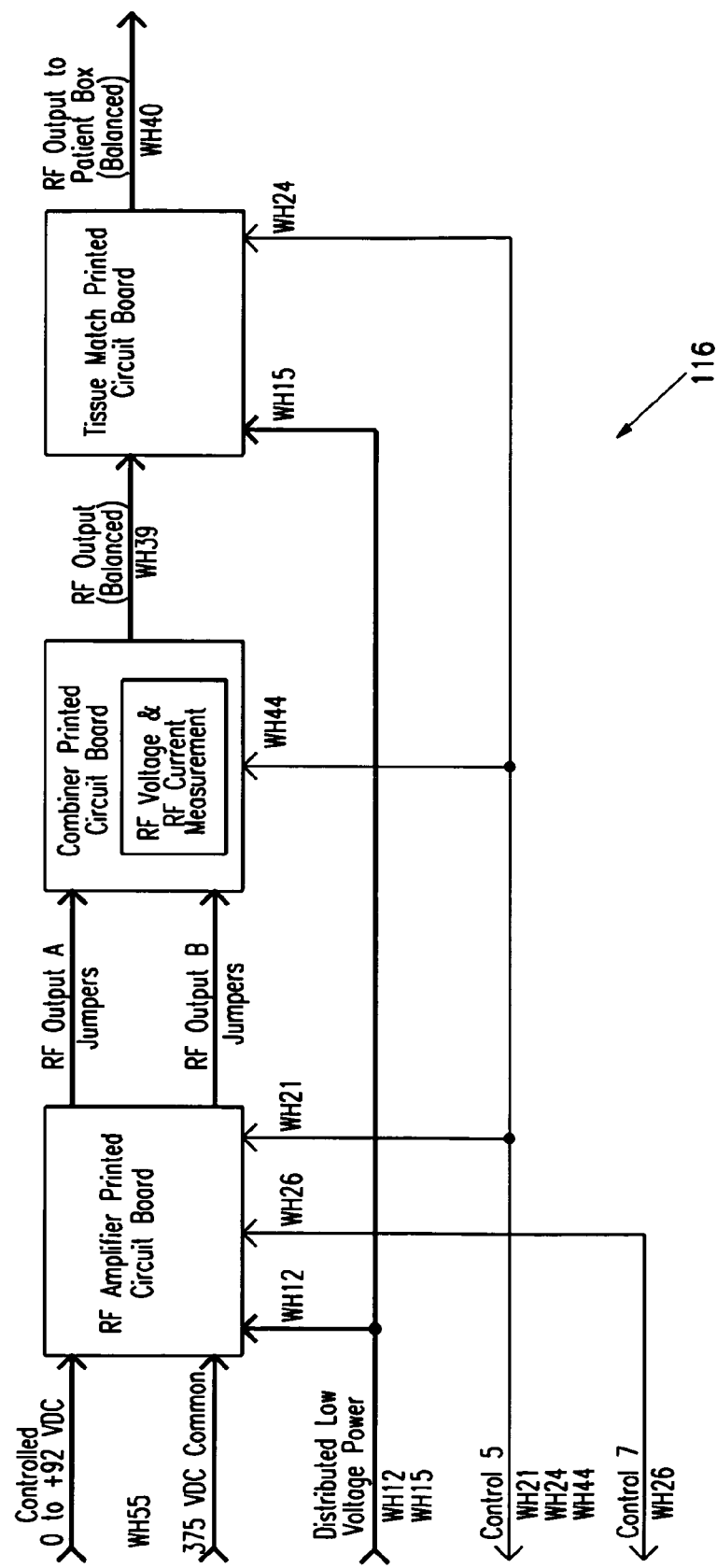
FIG. 7 is a block diagram of the RF amplifier of the electrosurgical generator system of the invention.
Figure 8:
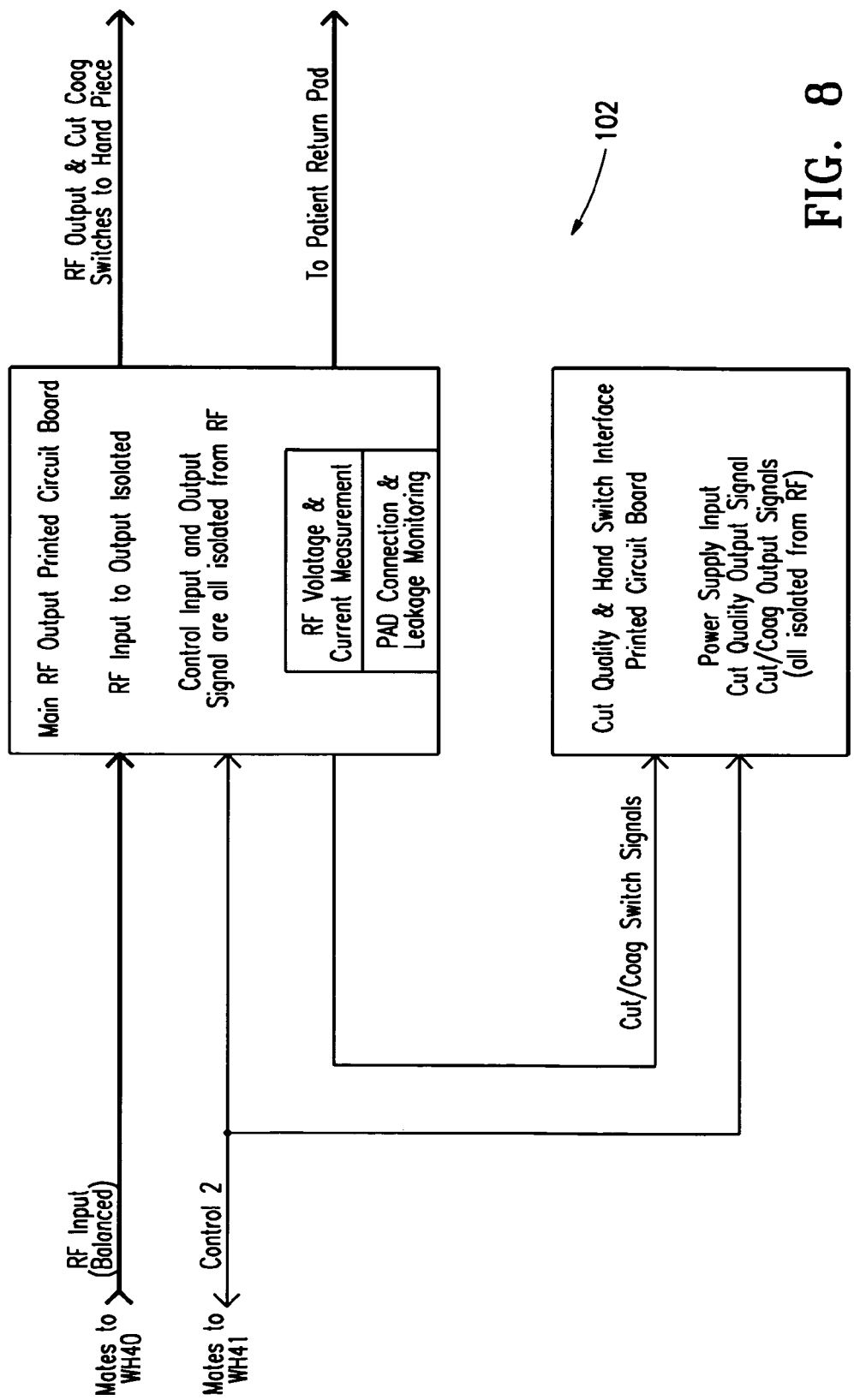
FIG. 8 is an exemplary block diagram of the patient box of the electrosurgical generator system of the invention.
Figure 9:
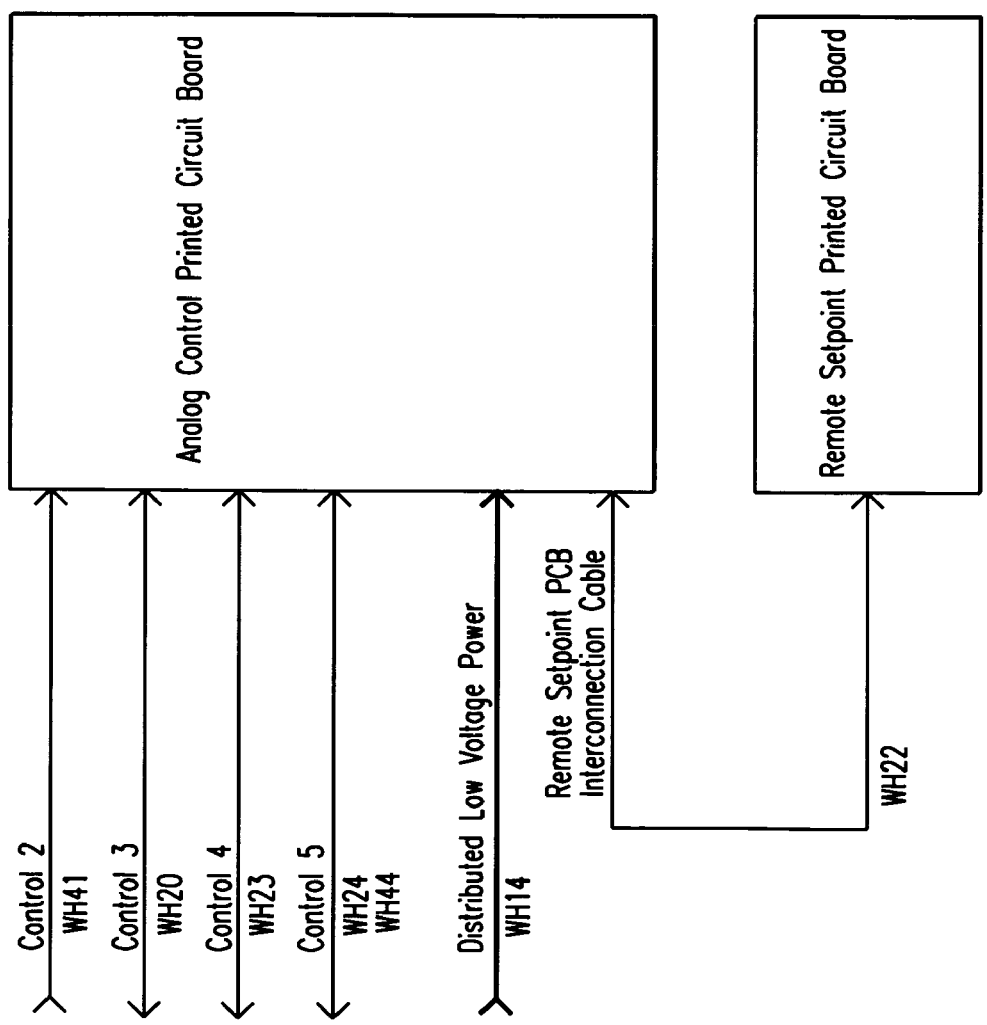
FIG. 9 is a block diagram of the analog control system of the electrosurgical generator system of the invention.
Figure 10:
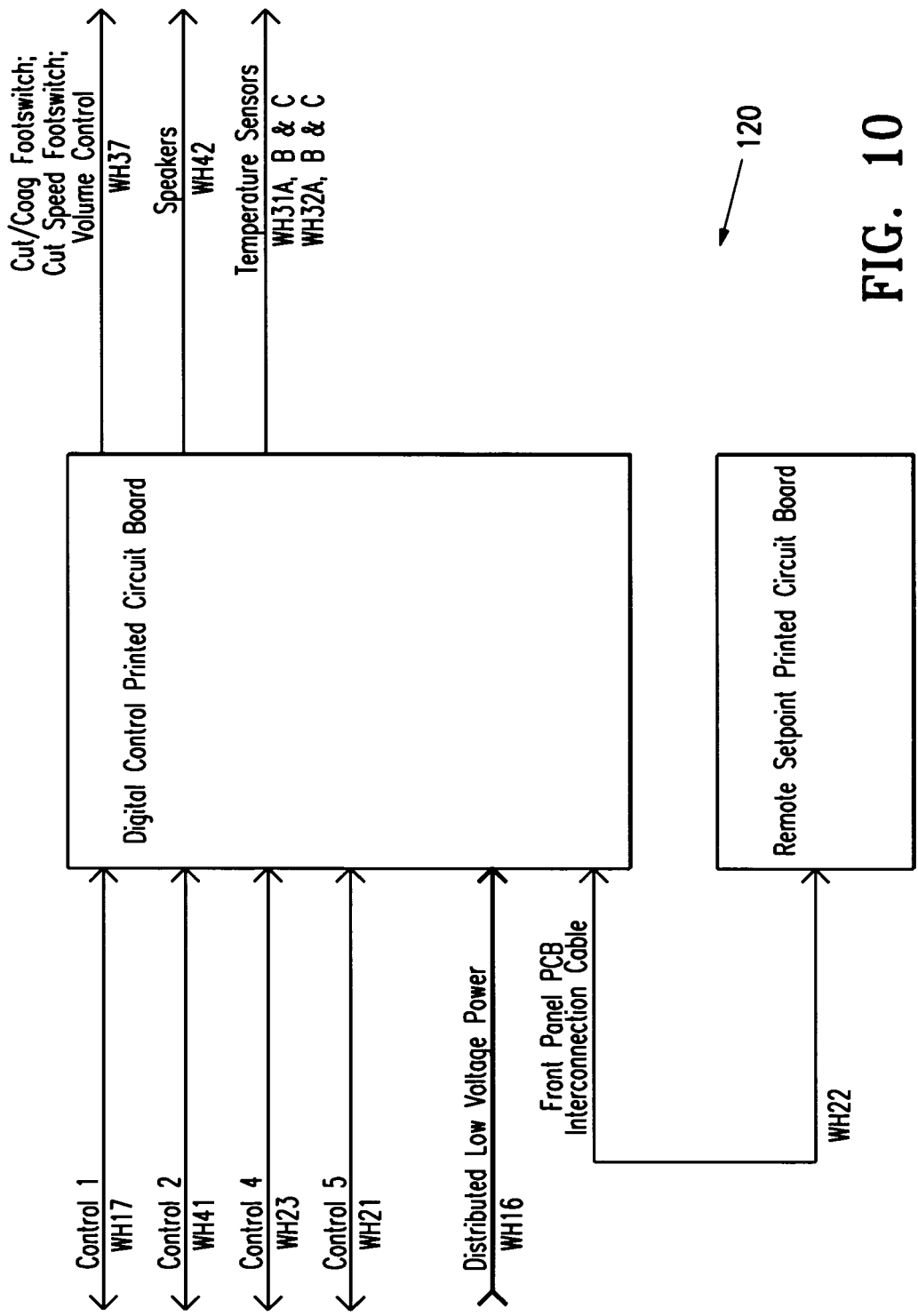
FIG. 10 is a block diagram of the digital control system of the electrosurgical generator system of the invention.

FIG. 3 shows an overall block diagram of the system and FIGS. 4-10 are block diagrams showing further details of the components represented by blocks in the block diagram of FIG. 3. FIG. 3 shows electrosurgical generator 100, patient box 102, RF outputs 104 and 106 and line-in 108. Electrosurgical generator 100 is an RF generator and is coupled to patient box 102 by lines 110. RF output 106 is supplied to the electrosurgical electrode (not shown) and RF output 104 is supplied to a return electrode (not shown). Within electrosurgical generator 100 are: Input Power Conditioning and Isolation System 122; RF Amp Power Supply 112; B+ Modulator 114; RF Amplifier 116; Analog Control System 118; and Digital Control System 120. FIG. 4 is a block diagram showing further details of Input Power Conditioning and Isolation System 122. FIG. 5 is a block diagram showing further details of RF Amp Power Supply 112. FIG. 6 is a block diagram showing further details of B+ Modulator 114. FIG. 7 is a block diagram showing further details of RF Amplifier 116. FIG. 8 is a block diagram showing further details of Patient Box 102. FIG. 9 is a block diagram showing further details of Analog Control System 118. FIG. 10 is a block diagram showing further details of Digital Control System 120. Like labels denote like features throughout the drawings and control lines Control 1-Control 7 indicate connections and controls between the sub-systems as appear in FIG. 3 and in FIGS. 4-10. As shown in FIG. 1, electrosurgical generator 100 and patient box 102 of FIG. 3, are disposed in separate housings (represented by features 2 and 6, respectively, of FIG. 1).

The electrosurgical generator/electrode system may be used to perform various cutting/cauterizing operations on various patients and on tissue with various characteristics. The control system of the invention accommodates different characteristics of the material being cut and different modes of operation of the electrosurgical electrode. The scalpel/cutting/electrosurgical electrode will hereinafter be referred to simply as the electrode. When cutting tissue of a patient, different tissue impedances and different electrode contact areas affect the voltage and current required to cut tissue. Moreover, starting a cut is a different process than cutting and advantageously utilizes different control parameters. Whereas a typical ESG does not distinguish between a start mode for starting a cut and a cut mode during which cutting takes place, and has no controls for these different modes of operation, the electrosurgical generator of the invention differentiates between such operational modes and supports substantial flexibility and programmatic control over the different requirements associated with the different modes. As shown in FIG. 3, the output of the inventive electrosurgical electrode is controlled by adjusting the DC voltage applied to the output stage of RF amplifier 116 (Control 5). This sets the output voltage of the electrosurgical generator when a high impedance load is connected. Lower impedance loads cause the RF output voltage to drop due to the internal impedance of the RF amplifier circuitry. This is true for any amplifier type and is typical for an electrosurgical generator. To keep the RF output constant with different output loads, a servo system is used to adjust the applied DC voltage to maintain the RF output during run or cut mode but not during start-to-cut, i.e., startup mode. In one exemplary embodiment, the RF output may be maintained at a constant level. This portion of the control system is the voltage servo, and represents a departure from conventional electrosurgical generator technology.

Different tissue types have different impedances and it has been found that high impedance tissue requires higher cutting voltages than low impedance tissues, however, applying excessive voltage for a given tissue type results in arcing and sputtering at the cutting electrode. Automatically limiting the RF output current reduces the RF output voltage when low impedance tissue is encountered by the cutting electrode. To account for these effects, the RF electrosurgical generator of the invention provides a current servo system which serves to adjust the DC input voltage to the RF amplifier to maintain the desired RF output current and duty cycle. Tissue impedance is measured indirectly by measuring the voltage, current, and the phase angle between the voltage and current signals in the RF output.

Some tissue types require a high RF output voltage but do not require high average power to sustain cutting. Simply controlling the RF output voltage and current, however, is not sufficient to support all tissue types and combinations of tissue types. The electrosurgical generator addresses this problem by controlling the RF output duty cycle. This parameter of the RF electrosurgical generator is user selectable over the range of about 15% to 40%. Changes in the RF output duty cycle are perceived as physical drag at cutting electrode. Higher duty cycles have less drag and allow for more rapid cutting than lower duty cycles. As such, this control of the duty cycle may be considered and referred to as "cut speed". The duty cycle may be defined as the ratio of the pulse duration to the pulse period. The RF electrosurgical generator also provides a coagulate, or simply "coag" mode which makes use of an even shorter 10% duty cycle which does not deliver sufficient power for effective cutting in one exemplary embodiment.

The electrosurgical generator of the invention differentiates between a start mode and cut mode. During active cutting, the cutting probe 16 of the electrosurgical electrode is surrounded by a plasma, at location 19 proximate cutting probe 16 as referred to in FIGS. 2A-2C. Prior to the start of cutting, the electrode, i.e. cutting probe 16, is in direct contact with tissue and the impedance is considerably lower than during cutting. Initiating a cut while in direct contact with tissue requires much more power than required during a cutting operation, i.e. it requires much more power than to sustain a cutting operation. The inventive RF electrosurgical generator has a user selectable start mode which selects different control parameters than cutting control parameters. In start mode, typical control settings would include a lower RF voltage output and a much higher current. Additionally, when start condition is detected, a matching network is inserted into the RF feed to improve the ability of the RF electrosurgical generator to deliver power to the substantially different impedance present during start. This network is switched out once successful startup has been detected and the generator moves to cutting mode. During cutting mode, the matching network is not used: rather; a server control system is used. In one exemplary embodiment, startup mode may include a preprogrammed duty cycle that is higher than would be used during cutting, for example in the 50-100% range. As above, during cutting mode, the selectable duty cycle may advantageously be within the range of 15% to 40%.

The electrosurgical generator includes a safety system. The safety system detects when the control system demands more power than the RF amplifier can deliver. This may indicate a fault in the control system or a problem with calibration. The control system supports another control parameter: RMS (root mean squared) DC input current to the RF amplifier. Peak current is not a reliable indicator of output power because it is dependent on the output duty cycle. Short duty cycles have a disproportionately high peak current. The DC current servo limits the RF output voltage to keep the DC current below the maximum set point. This allows short term maximum RF output power to any low impedance load. In one embodiment, the control system monitors DC current independent of the other control modes selected. In one exemplary embodiment, the control system only comes into effect when the RF amplifier is at its maximum limit, although lower set points may be used in other exemplary embodiments.

The control system of the invention functions to keep the total integrated power output of the electrosurgical generator below a prescribed maximum power such as 400 Watt-seconds in an exemplary embodiment. A separate safety monitoring circuit is provided which prevents the 400 Watt-second limit from being exceeded, however the control system itself is designed to limit power output. The full power, e.g. 1200 Watt output power and/or 100% duty cycle, may be made available in start mode only. Other maximum power values may be used in other exemplary embodiments. Applicants have determined, however, that in various exemplary embodiments, lower output duty cycles such as a 50% output duty cycle is as effective in starting as a 100% duty cycle. As such, the average power output may alternatively be reduced to half-maximum power, e.g., 600 Watts. Instantaneous power, e.g. 400 Watt-seconds, may be maintained as this parameter critically controls cutting operations. To limit the total power output joint start mode, the start mode may be time-limited. For example, the start mode may be limited to 600 milliseconds in one exemplary embodiment.

The electrosurgical generator of the invention detects when a cut has started and switches from start mode to cut mode when such is detected. A DC voltage appears across the RF outputs (cutting electrode and return electrode) as a result of plasma forming on the cutting electrode. This DC voltage signal is used to determine how effectively an electrosurgical generator is cutting, as well as when the cut has started. The inventive electrosurgical generator includes a control system that monitors the level and polarity of this DC voltage signal and determines when cutting has started. The control system then switches modes when cutting has started. The DC voltage system may be referred to as a "cut quality signal". In other exemplary embodiments, the switch between modes may be made responsive to the associated tissue impedance change when cutting starts. According to this exemplary embodiment, the voltage and current outputs are monitored and the impedance calculated. The aforedescribed cut quality signal is used by the control system. Once the electrosurgical generator/electrode system has entered cut mode, the control system uses a servo system to maintain the cut quality signal above a minimum level. The minimum level may be preselected. In this manner, the electrosurgical generator may use the lowest amount of power required to continue cutting. This, in turn, results in the least amount of tissue damage due to heating or overheating. The cut quality signal can become quite large in some tissue types. To avoid this from causing the RF output voltage to drop to such a low level that cutting would stop at the next tissue boundary, the electrosurgical generator of the present invention provides a minimum voltage output limit while operating in cut quality servo mode, described above. The minimum RF voltage output is set such that the plasma never quenches.

As described above, the configuration of the inventive electrosurgical generator enables a system that provides a very high power output. The extra power is put to use via a complex control system that works with various, different tissue types and the electrosurgical generator has a start mode that advantageously makes full use of the output power. The electrosurgical generator can detect when tissue cutting has started and switch the control system from a start up mode that uses a matching network to a run mode controlled by a servo system.

Each of the control inputs or telemetry used by the electrosurgical generator, for example RF voltage, RF current, cut quality signal, etc., are available for use by an external system. These signals are intended for use for expanding internal functionality such as tissue matching as will be discussed, or to provide feedback to a further surgical device. The telemetry signals can be galvanically isolated to facilitate monitoring operation when the electrosurgical generator/electrode system is coupled to a patient.

The electrosurgical generator/electrode system of the invention is compatible with robotics. When a robotic system is utilized, it does not have the same tactile feedback that a human operator has. In this embodiment, several of the telemetry signals may be used directly or further processed to determine how the system is performing. In one embodiment, the telemetry signals may provide detail as to the kind of tissue being cut, and the transition from one tissue type to another, for example from healthy tissue to cancerous tissue. This information may be displayed or fed back into the robotic system. For example, when cancerous tissue is being removed, it is important that immediately adjacent healthy tissue is also removed as a safeguard.

Figure 15:
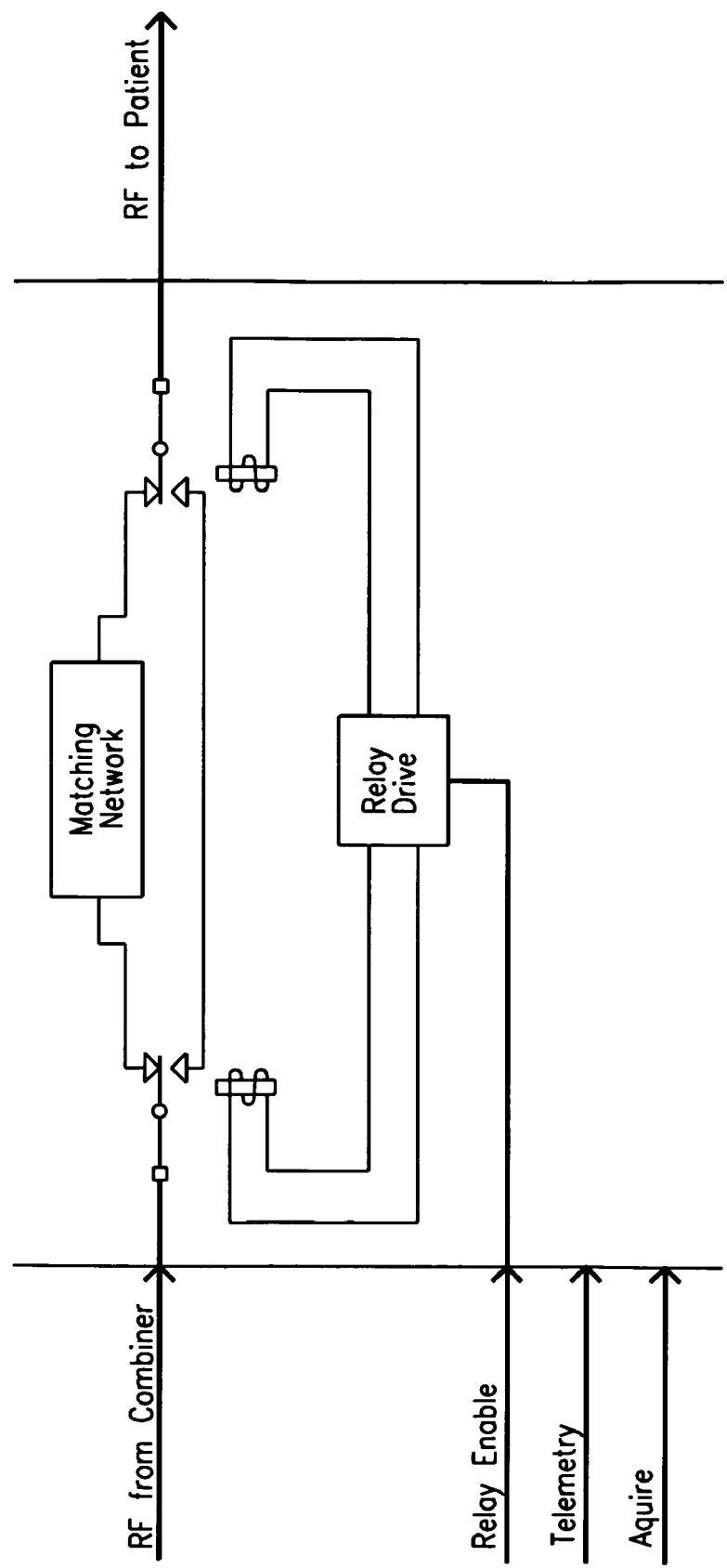
FIG. 15 is a block diagram showing the tissue matching capabilities of the RF electrosurgical generator of the invention.

The electrosurgical generator of the invention provides a tissue impedance matching feature such that the output impedance of the RF amplifier matches the load impedance of the tissue to enable the transfer of maximum power to a load. The primary impedance match in the system is accomplished in the patient box RF transformer. Applicants have found that breast tissue, for example, has an impedance of about 450 ohms when cutting and have also found that a class D amplifier with a 350 ohm transformer can effectively match the detected tissue impedance. Impedance matching may alternatively be accomplished with reactive components. In start mode, when the system expects to start into low impedance tissue, a matching network is switched inline with the RF amplifier to provide a reactive match to the expected tissue impedance. This enables the electrosurgical generator to transfer more of the RF output power to the tissue, allowing an efficient start. Once tissue starting has been accomplished, the matching network is switched out of circuit. The matching network matches average expected tissue impedances. Output voltage, current and phase is measured and actual tissue impedance calculated therefrom. Once the tissue impedance is known, an exact matching network is selected either by selecting from a number of fixed networks or by using variable networks that are tuned as required. The electrosurgical generator/electrode system measures RF parameters voltage, current and phase at two different locations in the system: at the point of load in the patient box and at the output of an RF combiner as are shown in FIG. 15. The matching network is advantageously located at the output of the RF combiner.

Leakage is mitigated in the RF electrosurgical generator/electrode system as described above. Leakage currents are currents that can return to earth ground from the output of the device and include a galvanic path to ground and capacitive, inductive and radiated pads to ground at high frequencies. The magnitude of the current flowing in these pads is directly proportional to the operating frequency and output power. Since the two RF output signals have opposite phases as described above, the leakage currents largely cancel. Any unbalanced signal results in a common mode signal which would be the only leakage current. The patient box employs a common mode choke in series with the output to further reduce RF leakage. This choke, shown in FIG. 16, and discussed infra, does not affect the differential output applied to the patient, but provides a high impedance path to any leakage current.

The design of the common mode choke is critical to prevent the introduction of shunt capacitance to the output circuit which results in significant impedance mismatch to the load being applied to the patient. The common mode choke includes an output winding and a return winding, each wound about a ferrite core. The output winding and return winding are spaced apart and in parallel to maintain the desired impedance. The output winding includes a wire carrying the outgoing RF signal and the return winding includes a duality of intertwined wires. Each winding includes the adjacent ribs spaced apart. The winding is kept symmetrical to maximize a balanced nature of the choke and the slotted rectangular ferrites are coupled to form the core. Input and output connections are physically separated to reduce the coupling from input to output. The physical design of the patient box that contains the common mode choke is also balanced as any asymmetry in the patient box induces a common mode path that contributes to leakage. The patient box includes the main RF power connection and several control and telemetry signals and all of the components of the main RF power path are physically arranged as symmetrically as possible which equalizes the capacitive coupling to the patient box enclosure which is grounded. The telemetry signals are connected via a balanced circuit. To further mitigate leakage, the push button interface for hand piece cut and coags control has extreme isolation to prevent further leakage. The section of this circuit that connects to the hand piece is battery powered to provide galvanic isolation from the rest of the patient box circuitry. The cut and coag signals are transmitted via fiber optic cable, as conventional optical isolation integrated circuits have been found to include too much capacitive coupling to allow for their use.

The system of the invention also provides for leakage path detection. The cutting and return electrodes connected to the patient box are widely separated during operation. For example, the cutting electrode may be used to cut cancerous breast tissue while the return electrode is in contact with the patient's buttocks. Other arrangements may be used in other exemplary embodiments and the cutting electrode may be used to operate on any part of the patient's anatomy. The electrodes cause a significant amount of common mode current to flow which exposes the patient to the risk of leakage by contacting a grounded piece of equipment. One way to reduce such potential leakage currents is to reduce the output level of the electrosurgical generator. The invention also provides an active monitoring circuit to detect a leakage current path. When the circuit detects a leakage path, it disables and turns off the output of the electrosurgical generator and sounds an alarm.

The leakage path detection system of the invention uses a test frequency much lower than the frequency of the output signal, e.g. 5 megahertz and much higher than the main frequency, e.g. 60 Hz. In one exemplary embodiment, the test frequency may be 500 KHz, but other frequencies may be used in other exemplary embodiments. The leakage path detection circuit monitors the leakage path to ground. In order to accomplish this, the detection circuit must be referenced to ground without causing a leakage path. The inventive system accomplishes this by connecting a small value capacitor from the center tap of the RF output transformer to ground. In one exemplary embodiment, the capacitor may have a 50 picofarad capacitance, but other capacitance values may be used in other exemplary embodiments. Since this connection is made at the center tap, it does not unbalance the RF output and does not contribute significant leakage current.

The test signal is induced onto the output of the patient box using a transformer. The secondary winding of the transformer is a balanced winding of both RF output leads. It may be similar to a common mode choke. When either of the two RF output leads, i.e. the cutting electrode and return electrode comes in contact with ground, current flows in the leakage path circuit which is detected by a pair of current transformers. Two transformers are used to form a redundant circuit, eliminating a possible single point failure. Additionally, the drive signal is continuously monitored for proper operation. This eliminates the drive signal as a possible source of failure. The leakage detection drive is inactive until RF output is requested and delivered. When this occurs, the leakage detection drive circuit is activated and the circuit tests for the presence of a leakage path. If no leakage path is detected, the RF output is enabled. The leakage detection circuit remains active while RF output is active, providing detection while the electrosurgical generator is in use. When the circuit does detect a leakage path, the RF output is turned off and an alarm optionally sounded.

FIGS. 11-17 are schematic block diagrams illustrating various systems of the invention. Each is intended to be exemplary and not restrictive of the invention.

Figure 11:
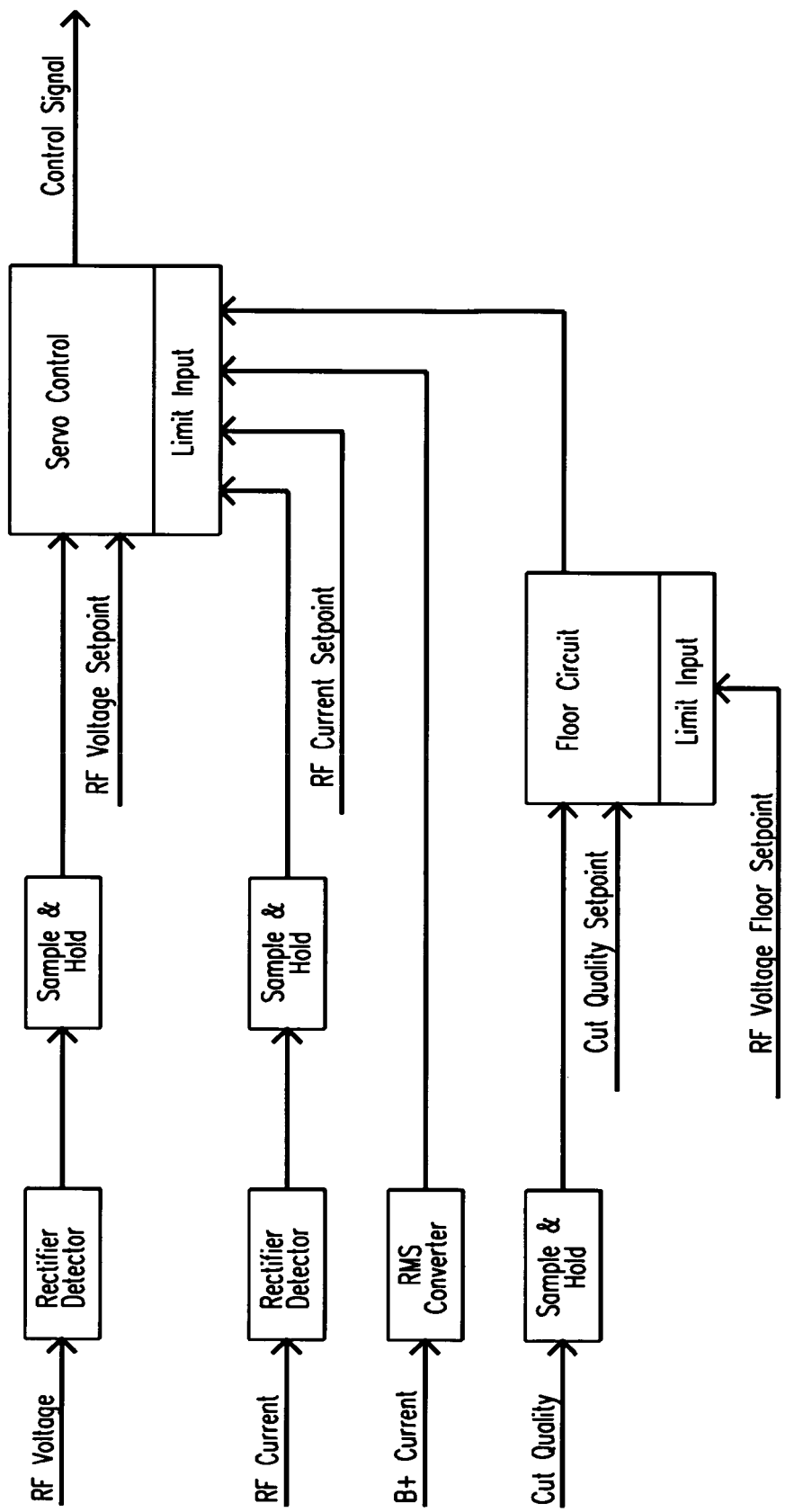
FIG. 11 is a block diagram of the control servo system of the electrosurgical generator system of the invention.

Referring to the control system servo block diagram in FIG. 11, the electrosurgical generator has several functional blocks that make up the control system. The exemplary servo block is one of these functional blocks. The servo block in its simplest form makes an output control voltage based on a setpoint and a feed back signal. In the case of the electrosurgical generator there is one main servo circuit to control the RF voltage output level. This circuit has additional limit inputs that can be used to reduce the RF voltage based on different parameters. The setpoints for voltage, current and cut quality are selected by digital logic from a preset array of 4 setpoints. The B+Current and RF Floor setpoints have only one setting each.

The main servo feedback signal is the RF output voltage as sensed by the patient box. In general this signal and its setpoint are used to set the maximum RF output voltage required. In many instances operating the electrosurgical generator at the maximum RF output voltage is not possible due to circuit limitations, or not required for the type of tissue being cut. Circuit limitations are for the most part related to the maximum power capability of the RF power amplifier and the maximum power capability of the RF power supply. Since the maximum RF output voltage and power supply voltage are both known, power can be controlled by limiting either the RF output current, or the power supply current. Proper selection of the control setpoints allows the electrosurgical generator to operate in a controlled manner at the maximum RF output power.

The RF Voltage and RF Current output of the Patient Box are rectified and detected by the Analog Control PCB to make pulses proportional to the voltage and current. The pulses are applied to sample and hold circuits which may advantageously hold the value constant between pulses. This produces a continuously varying signal proportional to the RF voltage and current. Thus the servo circuit works with smoothly varying signals so that the RF output is consistent from pulse to pulse.

The power supply current is sensed by the B+Modulator. This current output has a complex wave shape, as the current draw is not continuous due to the RF output duty cycle. The current output is applied to an RMS voltage convert on the Analog Control circuit board before it is used as a control input. The RMS value is directly proportional to the output power of the power supply.

The cut quality signal is produced by the RF output pulses, but does not have an RF component. The signal is applied to a sample and hold circuit as described above for the voltage and current. Since the cut quality signal can lag behind a change in tissue type, the cut quality signal could reduce the RF output voltage to the point that cutting might stop. For this reason an RF Voltage output Floor setpoint is used to keep the RF output above a minimum level.

Figure 12:
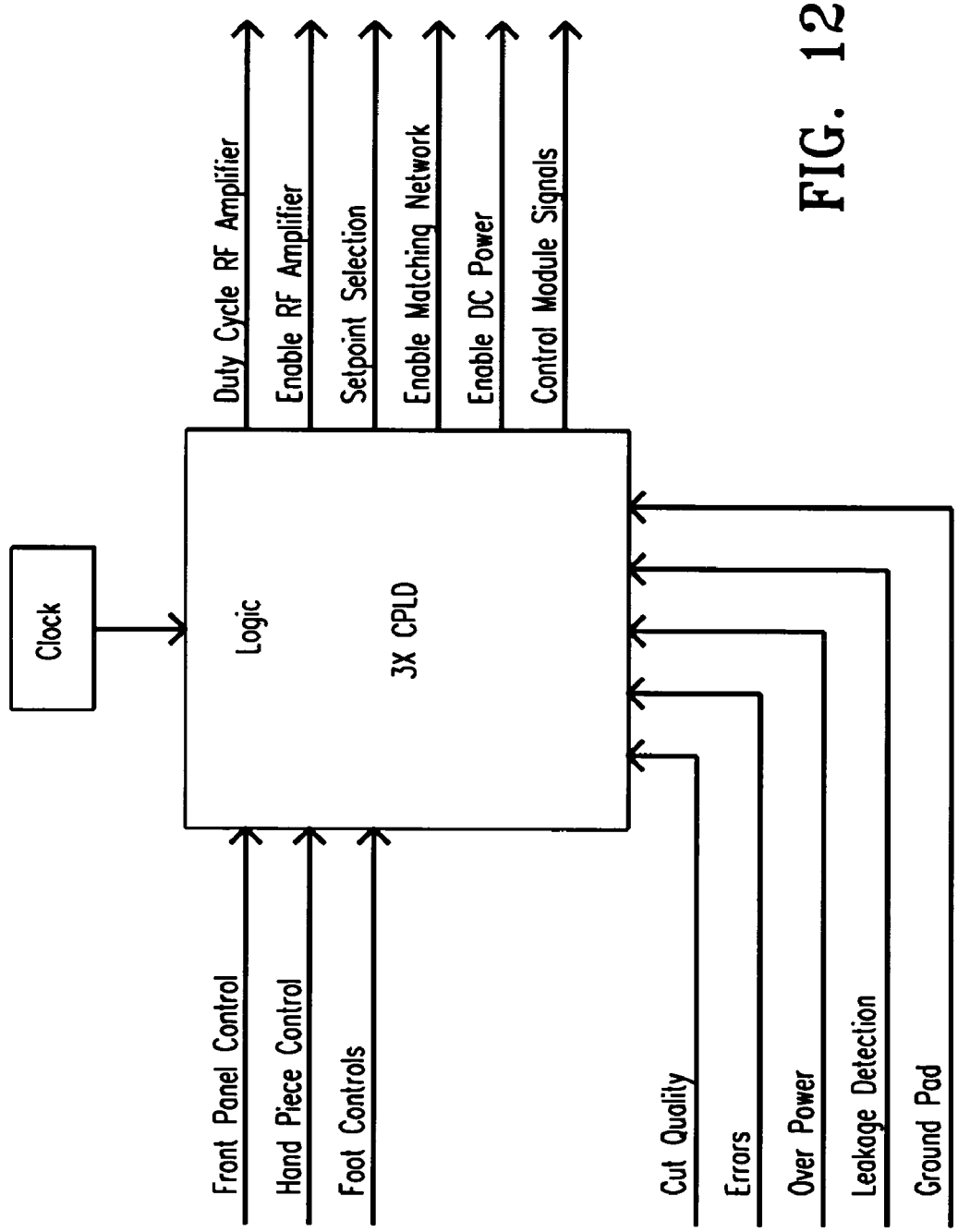
FIG. 12 is a block diagram of the control logic system of the electrosurgical generator system of the invention.

Referring to the Control Logic Block Diagram of FIG. 12, the electrosurgical generator control logic regulates the operation of the RF amplifiers by selecting the setpoints of the servo controls, selecting the duty cycle, and switching the matching network. Preset control settings may be selected by the user via front panel controls and foot switches. Operation of the electrosurgical generator is enabled via foot switch or hand controls. Any detected circuit faults are reported to the control logic as errors that will either inhibit operation, or turn off the RF output. Turning on the RF output requires that several subsystems be enabled. This acts as an interlock preventing a single point failure from producing uncontrolled RF output.

The electrosurgical generator control logic is implemented in 3 CPLDs. The CPLD are electrically reprogrammable and the control functions and their interactions can be changed. The description here is of the exemplary illustrated logic configuration of FIG. 12. Other configurations can be utilized to make use of the electrosurgical generator features in different combinations.

The control logic generates the output duty cycle, and selects the preset servo control set points. The matching network can also be switch in or out of circuit as described supra. The current electrosurgical generator setting allows the selection of eight different Cut duty cycles from 15% to 40% in one exemplary embodiment, as well as enabling start mode. The Coag duty cycle is fixed at 10% in one exemplary embodiment. Duty cycle is controlled as "Cut Speed" selected by either front panel control or by foot switch control. Start mode can only be selected from the front panel.

In the electrosurgical generator, start mode is intended to be a high RF output power mode coupled with use of a matching network. The control logic selects the servo presets associated with start mode. Since start mode may be limited to 600 milliseconds of operation in one exemplary embodiment, more power can be safely allowed than in normal operation. The transition from Start mode to normal operation is triggered by the Cut Quality signal exceeding a setpoint. In normal operation the matching network is switched out of the RF output path, and the lower power Run servo presets are selected.

There are several safety related signals and systems monitored by the control logic. These include status from all the PCB in the system as well as control signals that are out of bounds. This includes the temperature sensors. All of these control signals are indicated in the block diagram as errors. The over power signal indicates that the calculated output power exceeded 400 Watt-Seconds according to the embodiment in which 400 Watt-Seconds was the maximum power. Other power maximums may be used in other exemplary embodiments, however. The leakage detect signal indicates that a leakage path to ground has been detected. The ground pad signal indicates that the ground pad is properly connected to the electrosurgical generator. If an error or fault is detected before RF power is turned on the electrosurgical generator is inhibited. If an error or fault is detected while RF power is on, the electrosurgical generator alarms.

The electrosurgical generator can be connected to a control module such as the CM 3000 control module manufactured by SenoRx, Inc., of Aliso Viejo, Calif., via the foot switch connector. Other control modules may be used in other exemplary embodiments. The control module can command the electrosurgical generator with the Cut or Coag inputs. In addition the control logic outputs two status lines to the control module. One status line is used to indicate that the electrosurgical generator has power on and ready to deliver RF power. The other status line is used to indicate that the Cut Quality signal present and that the electrosurgical generator has completed the start function in start mode. This signal indicates that cutting is taking place and that the control module can move the cut electrode.

Figure 13:
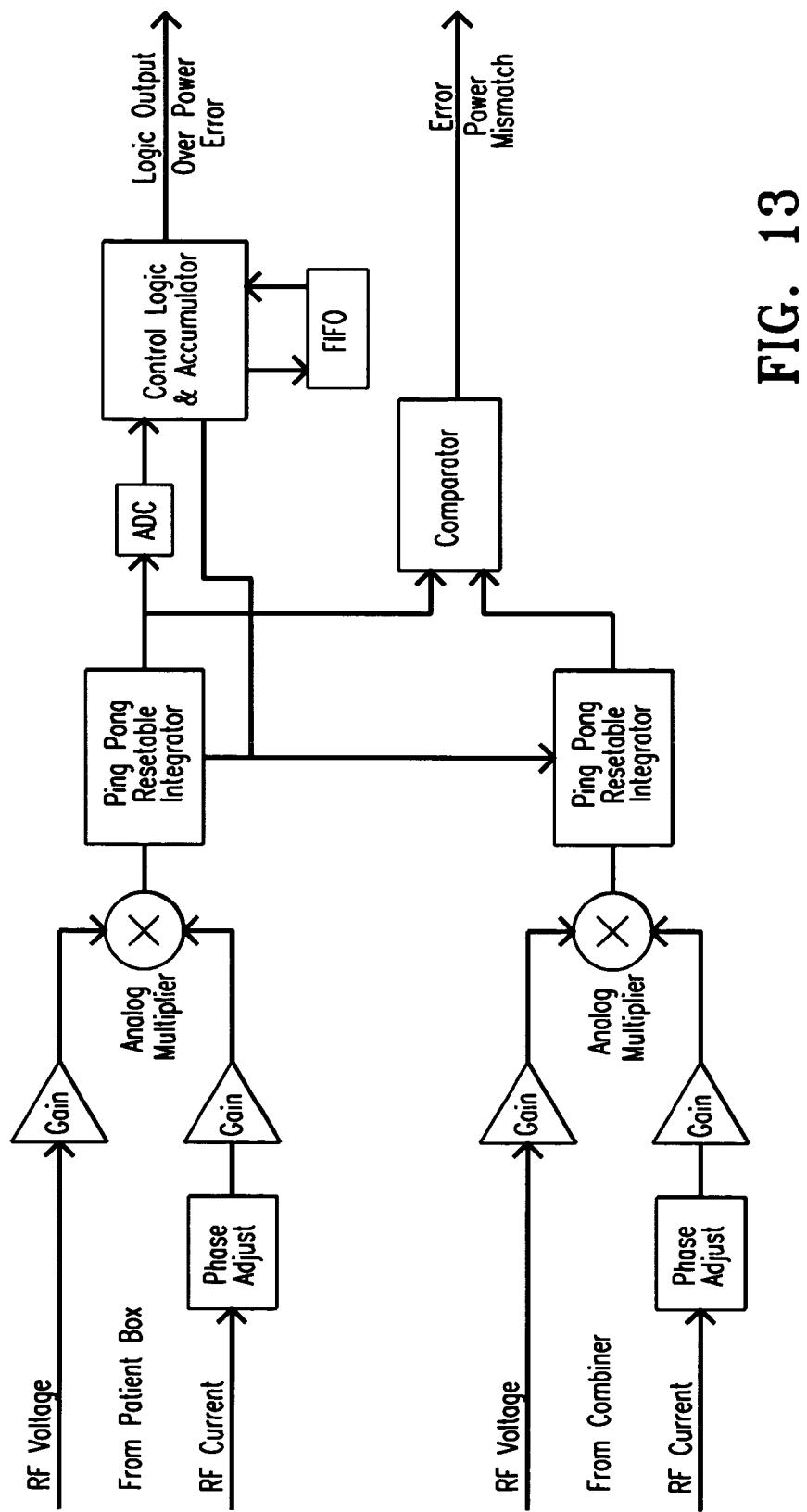
FIG. 13 is a block diagram showing power calculation for the RF electrosurgical generator of the invention.

Referring to the Power Calculation Block Diagram of FIG. 13, the electrosurgical generator limits the average RF output energy to 400 Watt Seconds to meet the IEC requirements for an electrosurgical generator, in one exemplary embodiment in which the instantaneous power can be greater than 400 watts, and can be as much as 1200 watts. The power output is controlled by selecting the servo set points and duty cycle limits, and is not expected to exceed the 400 Watt Second limit. The total power output is monitored continuously to guard against control circuit failure. The circuit calculates Watt Seconds directly, avoiding any complications resulting from indirect measurements and approximations.

The RF telemetry signals from the Patient Box are used to calculate the RF output energy as these are measured in 2 locations including advantageously closest to the patient connection as is most accurate. The RF telemetry from the combiner is used to monitor RF output energy. The two measurements are compared and must agree within a preset tolerance or an error is generated. This comparison adds a redundant check on the Patient Box telemetry eliminating a potential single point failure causing uncontrolled RF output.

The voltage and current sensors and associated circuitry introduce unequal delays resulting in an unwanted phase shift between the voltage and current signals. A phase adjustment circuit is used to compensate for these differences. An adjustable gain amplifier is used to compensate for circuit component variations and make use of the full dynamic range of the analog multiplier increasing accuracy.

The output of the analog multiplier is the product of the voltage and current (Watts) which is integrated over time to calculate Watt Seconds. The exemplary integration period may be 1 millisecond after which the integrated value is digitized the analog to digital converter (ADC). After the ADC conversion the integrator is reset to zero ready for the next integration cycle. While one integrator is being digitized and reset a second integrator is performing an integration cycle. The output of the analog multiplier is "ping ponged" between two integrators to perform continuous integration.

The digitized result of the 1-millisecond integration is digitally accumulated over a 1 second interval to complete the Watt Second calculation. If the digital sum exceed 400 watt seconds an "over power error" is generated. In actuality the limit value is slightly less than 400 watt seconds to account for inaccuracies the calculation process, and the 1-millisecond sample interval.

The digitized integration value is also stored in a FIFO (first in first out) memory. One second old values are read out of the memory and subtracted from the accumulator before a new value is added in. Thus the accumulator is the sum of the integration values over the most recent one second period. No subtractions occur during the first one second of operation to initialize the FIFO memory. The power calculation circuitry runs continuously even when RF power is off. This avoids having to reinitialize the accumulator and FIFO memory.

Figure 14:
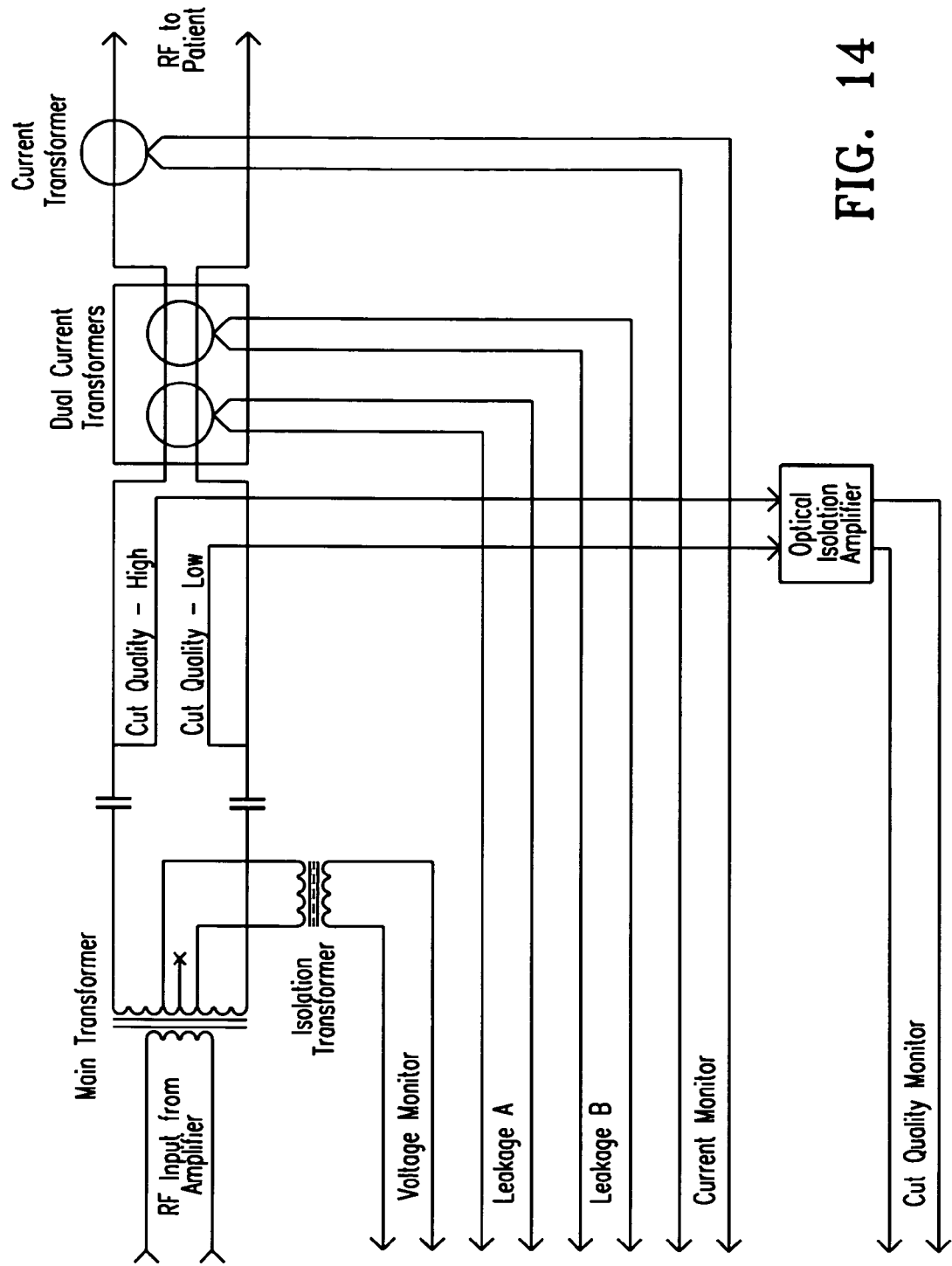
FIG. 14 is a telemetry block diagram for the RF electrosurgical generator of the invention.

Now referring to the Telemetry Block Diagram of FIG. 14, the telemetry for servo control and leakage current mitigation is taken from the Patient Box. The block diagram omits the common mode chokes and leakage drive for clarity. The main transformer is used to step up the RF voltage. This transformer is tapped symmetrically around the center of the secondary winding to provide a voltage proportional to the output voltage. This method is used rather than measuring the output voltage directly because it is a low impedance connection that is not easily unbalanced. The tapped voltage is further reduced by an isolation transformer before providing the final voltage output.

The leakage current monitoring circuit looks for an induced common mode current. Two current transformers are used to monitor the common mode current and provide isolation and balanced drive. Since this is a safety related feature two transformers are used to provide redundant measurement. The RF output current is monitored by a single current transformer. This transformer provides isolations and balanced drive for the telemetry signal.

Cut Quality is an essentially DC voltage produce at the cutting electrode. It is monitored before the isolation capacitors by a differential amplifier. The RF signal is removed with a low pass filter leaving only the Cut Quality signal. The filter output is used to drive an optically isolated amplifier that provides differential drive for the telemetry output signal.

Referring to the Tissue Match Block Diagram of FIG. 15, the tissue matching PCB is connected between the combiner PCB and the electrosurgical generator output to the Patient Box. In the present configuration the tissue match circuit includes two relays that are used to switch between straight pass through, and a single matching network. The matching network is only used in conjunction with start mode, and the relays are enabled by the control logic.

The output impedance of the Patient Box is 450 based on the output transformer. The 450 Ohm value is not selected to best match the tissue, but to give the most flexibility when used with the Class D amplifiers and the 100 Ohm balanced feed line. The tissue impedance is different when cutting than when starting, and has a lot of variation in both cases. The single matching network is selected to match the midpoint in the expected spread of start impedances.

Additional signals are brought out to the tissue matching circuit for possible future enhancements. These are the telemetry signals which include the voltage, current, and related phase angle. Both the voltage and current measured at the Patient Box, and at the combiner PCB are available. The telemetry can be monitored during a test RF pulse made at the beginning of start mode, while the relays are still in pass through mode. The acquire signal is to indicate when the RF test pulse is stable. Additional circuitry may be used to analyze the telemetry and select the best match from several matching networks. A closer match would allow more power transfer to the tissue and better starting.

Even in the exemplary embodiment with a single matching network, the electrosurgical generator still outputs the RF test pulse and acquires signals. Any future change to allow the selection of more than one matching network would only involve the Tissue Match PCB.

Figure 16:
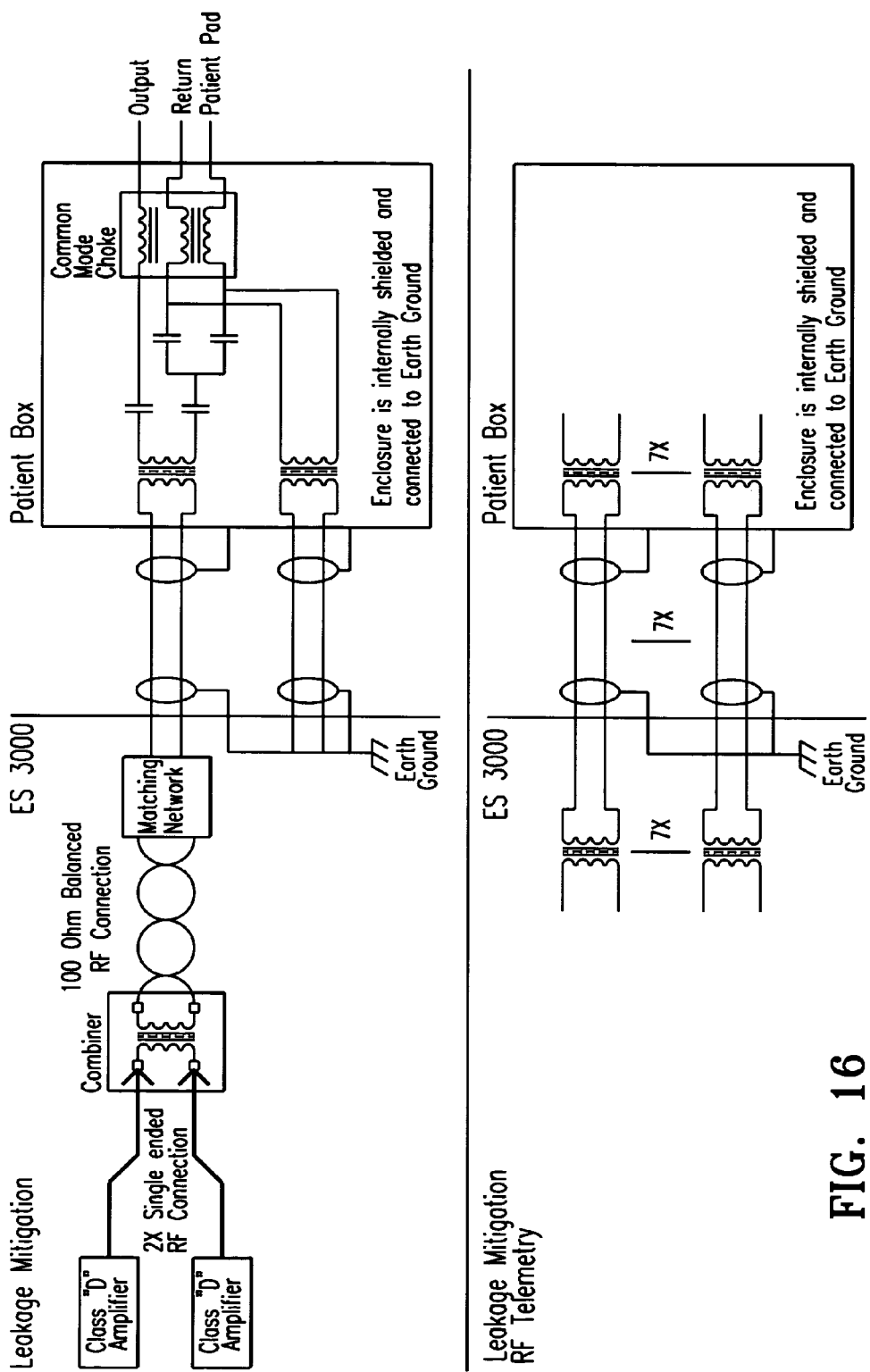
FIG. 16 is a block diagram showing the leakage mitigation system of the RF electrosurgical generator system of the invention.

Referring to the Leakage Mitigation Block Diagram of FIG. 16, since the electrosurgical generator is an RF device, two kinds of leakage current are a concern: low frequency mains currents and high frequency RF currents. The low frequency currents are mitigated with a mains isolation transformer and are not illustrated in the block diagram of FIG. 16. RF leakage current arises from unintended coupling of the RF output to ground. This coupling can be of any form, but the hardest to control are radiated and capacitive coupling.

The first step in militating against leakage current is to isolate the RF signal path from earth ground. This is accomplished in the electrosurgical generator by placing the active RF circuits on an insulated sub-chassis. The main leakage path to ground inside the electrosurgical generator is capacitive coupling. The RF circuits are made as symmetrical as possible. This forces the capacitive coupling to be symmetrical around earth ground causing the positive and negative halves of the RF signal to cancel out resulting in no net leakage current.

The inputs to the combiner are the two single ended RF amplifier outputs. These signals are single ended as the return current is carried through signal ground. The output of the combiner is a transformer with a balanced output. The input transformer of the Patient Box is also a transformer with a balanced input. Since the output is not ground referenced in any way, the RF output is naturally forced to shift until both of the RF output signals are symmetrical about earth ground. Since the signals are symmetrical around ground any leakage current is canceled. The receiving transformer only passes the intended differential signal and does not pass any common mode signal. Leakage current is for the most part a common mode current. The only mechanism for coupling common modes signals is primary to secondary capacitive coupling. The RF power transformers are fabricated with the primary and secondary windings wound in opposite directions (not parallel) to minimize capacitive coupling.

To preserve the balance output of the electrosurgical generator connection to the Patient Box, a 100 Ohm shielded balance transmission line is used in the illustrated, exemplary embodiment. The shield is connected to earth ground inside the electrosurgical generator. This transmission line is constructed such that both signal lines have identical capacitive coupling to ground. Again the symmetrical coupling cancels any leakage current. The Patient Box is shielded and connected to the shield of the transmission line and thus connected to earth ground. The circuits inside the Patient Box are made substantially symmetrical creating equal coupling to ground, thus minimizing leakage currents.

Any asymmetry in the RF output presents itself by as a common mode signal. The common mode choke inside the Patient Box blocks the flow of any common mode signal. This drives the leakage current to almost zero at the output of the patient box. The return path for leakage current through the Patient Box would also be common mode. The common mode choke also blocks this current path.

The Patient Box is not fully symmetrical in that it has two return electrode connections. These connections are used to verify the proper attachment of the return electrode. When in use these connections are at the same potential and can be electrically treated as a single wire. However, three physical wires must pass through the common mode choke. Proper fabrication of the choke is useful as parasitic inductance and capacitance can be introduced in the differential (intended) signal path if fabricated improperly. The common mode signal path must be as inductive as possible. Introducing parasitic elements in the RF signal path can cause an impedance mismatch resulting in reduced power output. The common mode choke is advantageously fabricated use two ribbon cable ferrite cores in one embodiment, allowing the conductor winding to be spread out uniformly reducing parasitic capacitance. The two return electrode wires are twisted together using 26 gauge wire and insulted with #18 Teflon sleeving. The output wire is 22 gauge and insulted with #20 Teflon sleeving. These values and material types are exemplary only. The three conductors are wound on the ferrite cores as if they were two conductors. This causes the coupling between the two return wires to be uniform and act as a single conductor at RF frequencies. The windings are parallel and evenly spaced to insure symmetry.

The RF telemetry signals between the Patient Box and the electrosurgical generator can also be a leakage current path. While the construction of the Patient Box is as symmetrical as possible, some telemetry signals by their nature are not symmetrical. The RF current monitor only measures the current on the RF output lead. While the ground pad monitor is connected only to the two return leads.

Most of the sensing is done before the common mode choke. This isolates the patient from the potential leakage path. The RF current sensor is fabricated to minimize the capacitive coupling between the RF output lead, and the sensor transformer. Furthermore all of the RF telemetry is transformer coupled at both ends. This forces the telemetry signals to be balanced and the leakage currents to cancel. The transformers at the receiving end on the Analog Control board reject any common mode signals, leaving capacitive coupling across the transformers as the only leakage path.

Figure 17:
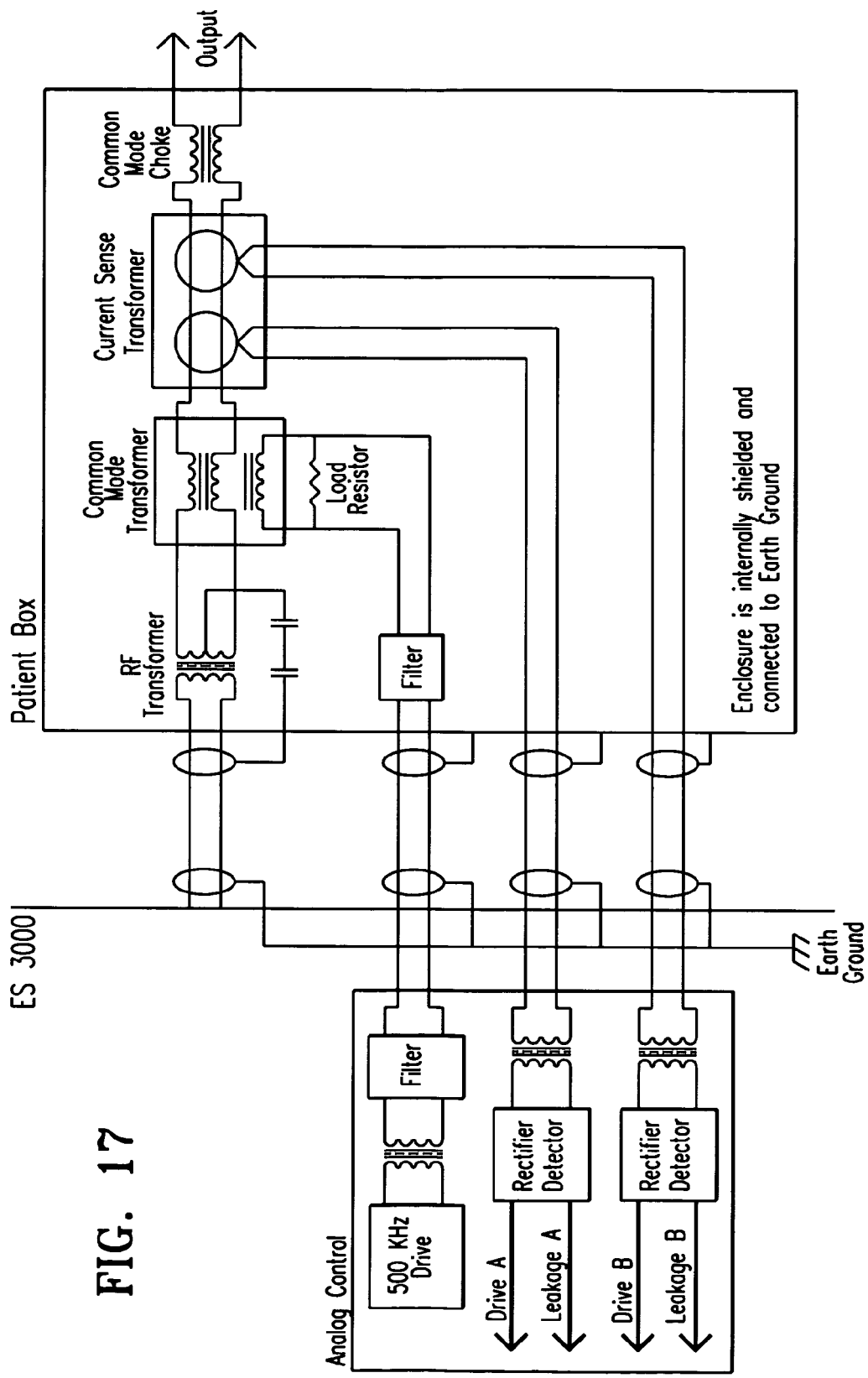
FIG. 17 is a block diagram showing leakage path detection capabilities of the RF electrosurgical generator of the invention.

FIG. 17 shows a Leakage Path Detection Block Diagram. With all of the leakage mitigation in place there is very little leakage current between the Patient Box and earth ground. This situation changes when leads are connected to the Patient Box outputs. A new leakage path may be introduced due to radiation of RF energy from the leads. The hazard exists due to the inadvertent contact between the patient and earth ground. Since the patient is directly connected to the Patient Box via the return electrode, leakage current can be measured at the Patient Box.

The inventive system is capable of operating at a frequency of 5 MHz and direct measurement of leakage current at the exemplary 5 MHz operation frequency is not effective. One method of mitigating a leakage current hazard is to determine a leakage current path. This would be an electrical connection between the output of the Patient Box and earth ground. Testing for this path is performed in the electrosurgical generator by inducing a test signal and looking for current flow. The test signal may be a 500 KHz AC voltage induced common mode on the Patient Box RF output leads. The test signal frequency is low enough to not be significantly attenuated by the common mode choke. Other test frequencies may be used in other exemplary embodiments.

A reference path to ground is created in the Patient Box by connecting two series capacitors to earth ground from the center tap on the secondary side of the RF transformer. Two capacitors are used to eliminate the potential for a single fault conduction creating a short to ground. By making a connection to the center tap of the transformer the output is still balanced.

A common mode transformer is used to induce the test signal onto the RF output leads. Since the test signal is equal on both leads none of the test signal current flows through the patient connected to the output leads. Two current sense transformers may be used to monitor for the presence of a common mode current indicating a leakage path. Since leakage detection is part of a safety system redundant measurement is required to eliminate the possibility of a single fault condition causing a failure of the leakage detection system.

The Analog Control PCB contains the circuitry to both drive the leakage path detection drive transformer and monitor the output of the current transformers. The drive circuitry may be a class D amplifier feed by an adjustable voltage source in the exemplary embodiment. This allows the drive level to be adjusted to compensate for circuit variations. A two stage filter is used to convert the square wave output of the class D amplifier to a sine wave. The first stage is on the Analog control PCB, and the second stage is in the Patient Box. The first stage low pass filters and helps match the output impedance of the amplifier to the transmission line. The second stage continues the filtering process and blocks any of the 5 MHz RF output induced in the common transformer. This eliminates another potential leakage path.

The output of the current transformers is rectified and detected converting the exemplary 500 KHz telemetry signal to a DC level proportional to the leakage current. Due to parasitic leakage paths in the Patient Box some small amount of leakage current is always detected when the drive signal is on. This low level signal is used by the Analog Control PCB to determine that the leakage path circuit is functioning properly. The drive signal and both current monitor circuits must be functioning for RF output to be enabled. If the leakage current increases beyond a setpoint while RF is on an alarm is generated and RF power is turned off.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as lower, upper, horizontal, vertical, above, below, up, down, top and bottom as well as derivatives thereof (e.g., horizontally, downwardly, upwardly, etc.) should be construed to refer to the orientation as then described or as shown in the drawing under discussion. These relative terms are for convenience of description and do not require that the apparatus be constructed or operated in a particular orientation. Terms concerning attachments, coupling and the like, such as connected and interconnected, refer to a relationship wherein structures are secured or attached to one another either directly or indirectly through intervening structures, as well as both movable or rigid attachments or relationships, unless expressly described otherwise.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A method for controlling an electrosurgical electrode of a medical device comprising:
   providing a patient box with a step-up transformer;
   providing an electrical conductor from said patient box in an electrical connection with said electrosurgical electrode of said medical device;
   providing an RF generator with a balanced and symmetrical shielded transmission line electrically connecting said RF generator to said patient box;
   delivering an RF energy from said RF generator to said patient box through said balanced and symmetrical shielded transmission line electrically connecting said RF generator to said patient box;
   monitoring an electrical characteristic associated with said electrosurgical electrode;
   controlling the RF energy from said RF generator based upon the monitored electrical characteristic associated with said electrosurgical electrode;
   delivering an RF signal with a first RF power level from said RF generator to said patient box;
   increasing said RF power level of said RF signal in said patient box;
   delivering said RF signal with an increased RF power level to said electrosurgical electrode as an RF output through the electrical conductor; and
   detecting a leakage current by inducing a test signal in said patient box by directing said RF signal through said step-up transformer in said patient box, said step-up transformer being an RF transformer coupling a series of two capacitors between ground and a center tap of a winding in said RF transformer, and inducing said test signal onto RF output leads of said patient box by passing said RF signal through a common mode transformer, said test signal having a frequency of about 500 KHz.

2. The method as in claim 1, further comprising monitoring said RF signal after passing through said RF transformer, using a plurality of current sense transformers.

3. The method as in claim 2, further comprising an analog circuit driving a leakage path detection drive transformer and monitoring an output of said current sense transformers.

4. A method for controlling an electrosurgical electrode of a medical device comprising:
   providing a patient box with a step-up transformer;
   providing an electrical conductor from said patient box in an electrical connection with said electrosurgical electrode of said medical device;
   providing an RF generator with a balanced and symmetrical shielded transmission line electrically connecting said RF generator to said patient box;
   delivering an RF energy from said RF generator to said patient box through said balanced and symmetrical shielded transmission line electrically connecting said RF generator to said patient box;
   monitoring an electrical characteristic associated with said electrosurgical electrode;
   controlling the RF energy from said RF generator based upon the monitored electrical characteristic associated with said electrosurgical electrode,
   wherein said patient box and said RF generator are disposed in separate housings, and further comprising:
   providing a common mode choke in said patient box housing, said common mode choke including an output winding and a return winding, each wound about a ferrite core, said output winding and said return winding spaced apart and in parallel to maintain a desired impedance, said output winding comprising a wire carrying an RF signal and said return winding comprising a duality of intertwined wires, each of said output winding and said return winding including adjacent ribs spaced apart and said output winding and said return winding being wound in opposite directions; and directing a common mode signal from said RF signal to said common mode choke thereby blocking said common mode signal while allowing said RF signal to be applied substantially unaltered to a patient.

* * * * *